United States Patent
Kise et al.

(10) Patent No.: US 10,400,311 B2
(45) Date of Patent: Sep. 3, 2019

(54) WROUGHT MATERIAL COMPRISING CU—AL—MN-BASED ALLOY EXCELLENT IN STRESS CORROSION RESISTANCE AND USE THEREOF

(71) Applicants: FURUKAWA TECHNO MATERIAL CO., LTD., Hiratsuka-shi, Kanagawa (JP); FURUKAWA ELECTRIC CO., LTD., Tokyo (JP); Tohoku University, Sendai-shi, Miyagi (JP)

(72) Inventors: Sumio Kise, Hiratsuka (JP); Toyonobu Tanaka, Hiratsuka (JP); Kenji Nakamizo, Hiratsuka (JP); Koji Ishikawa, Hiratsuka (JP); Misato Fujii, Hiratsuka (JP); Toshihiro Omori, Sendai (JP); Ryosuke Kainuma, Sendai (JP)

(73) Assignees: FURUKAWA TECHNO MATERIAL CO., LTD., Hiratsuka-Shi, Kanagawa (JP); FURUKAWA ELECTRIC CO., LTD., Tokyo (JP); TOHOKU UNIVERSITY, Sendai-Shi, Miyagi (JP)

( * ) Notice: Subject to any disclaimer, the term of this patent is extended or adjusted under 35 U.S.C. 154(b) by 779 days.

(21) Appl. No.: 14/997,185

(22) Filed: Jan. 15, 2016

(65) Prior Publication Data

US 2016/0130683 A1    May 12, 2016

Related U.S. Application Data

(63) Continuation of application No. PCT/JP2014/068400, filed on Jul. 10, 2014.

(30) Foreign Application Priority Data

Jul. 16, 2013 (JP) .................................. 2013-148058

(51) Int. Cl.
*G02C 5/00* (2006.01)
*G02C 5/08* (2006.01)
(Continued)

(52) U.S. Cl.
CPC .................. *C22C 9/01* (2013.01); *A61C 7/20* (2013.01); *A61F 5/019* (2013.01); *A61F 5/11* (2013.01);
(Continued)

(58) Field of Classification Search
CPC . G02C 5/00; G02C 5/003; G02C 3/04; G02C 5/006; G02C 1/08; G02C 1/04;
(Continued)

(56) References Cited

U.S. PATENT DOCUMENTS 6,406,566 B1    6/2002 Ishida et al.
2010/0228173 A1*    9/2010 Ishida ..................... A61F 5/11
602/31
(Continued)

FOREIGN PATENT DOCUMENTS

CN    101985729 A    3/2011
JP    2001-020026 A    1/2001
(Continued)

OTHER PUBLICATIONS

International Search Report issued in PCT/JP2014/068400 dated Oct. 14, 2014.
(Continued)

*Primary Examiner* — Dawayne Pinkney
(74) *Attorney, Agent, or Firm* — Birch, Stewart, Kolasch & Birch, LLP

(57) ABSTRACT

A wrought material containing a Cu—Al—Mn-based alloy, in which an existence frequency of a coincidence grain boundary with a Σ value of 3 or less is 35% or more but 75%
(Continued)

○:3 point of intersection or less, and which has a recrystallized microstructure substantially formed from a β single phase; and the use thereof.

8 Claims, 7 Drawing Sheets

(51) Int. Cl.
| | |
|---|---|
| *G02C 1/00* | (2006.01) |
| *G02C 1/08* | (2006.01) |
| *G02C 1/04* | (2006.01) |
| *G02C 1/02* | (2006.01) |
| *C22C 9/01* | (2006.01) |
| *C22C 9/05* | (2006.01) |
| *C22F 1/08* | (2006.01) |
| *A61C 7/20* | (2006.01) |
| *A61L 31/02* | (2006.01) |
| *A61L 31/14* | (2006.01) |
| *A61F 5/01* | (2006.01) |
| *A61F 5/11* | (2006.01) |

(52) U.S. Cl.
CPC ............. *A61L 31/022* (2013.01); *A61L 31/14* (2013.01); *C22C 9/05* (2013.01); *C22F 1/08* (2013.01); *G02C 5/008* (2013.01); *A61C 2201/007* (2013.01)

(58) Field of Classification Search
CPC ...... G02C 1/02; G02C 5/2209; G11B 7/0932; G02B 7/102; G02B 7/02; G02B 7/14; G02B 7/023; G02B 7/04; G02B 7/08; G02B 7/021
USPC ... 351/41, 53, 56, 63, 83, 90, 103, 110, 154, 351/107; 359/694, 811–830
See application file for complete search history.

(56) References Cited

U.S. PATENT DOCUMENTS

2013/0087074 A1* 4/2013 Araki .................. C22C 9/05
106/641
2013/0102942 A1 4/2013 Tanaka et al.

FOREIGN PATENT DOCUMENTS

| | | |
|---|---|---|
| JP | 2009-263784 A | 11/2009 |
| JP | 2011-168819 A | 9/2011 |
| JP | 5144834 B2 | 2/2013 |
| JP | 2013-087908 A | 5/2013 |
| WO | WO 2009/123136 A1 | 10/2009 |
| WO | WO 2011/129435 A1 | 10/2011 |
| WO | WO 2013/031841 A1 | 3/2013 |

OTHER PUBLICATIONS

Written Opinion of the International Searching Authority issued in PCT/JP2014/068400 dated Oct. 14, 2014 (PCT/ISA/237).
Chinese Office Action and Search Report, dated Nov. 30, 2016, for Chinese Application No. 201480040263.3, together with an English translation thereof.
Randle et al., "Mechanisms of grain boundary engineering," Acta Materialia, vol. 54, 2006 (available online Feb. 17, 2006), pp. 1777-1783.
Chinese Office Action and Search Report, dated Jul. 28, 2017, for corresponding Chinese Application No. 201480040263.3, along with an English translation.
Jiang et al., "Improvements of intergranular corrosion resistance and mechanical properties of brass H68," The Chinese Journal of Nonferrous Metals, vol. 21, No. 2, Feb. 28, 2011, pp. 377-383 (Total pp. 7), along with an English abstract.

* cited by examiner

○ : 3 point of intersection

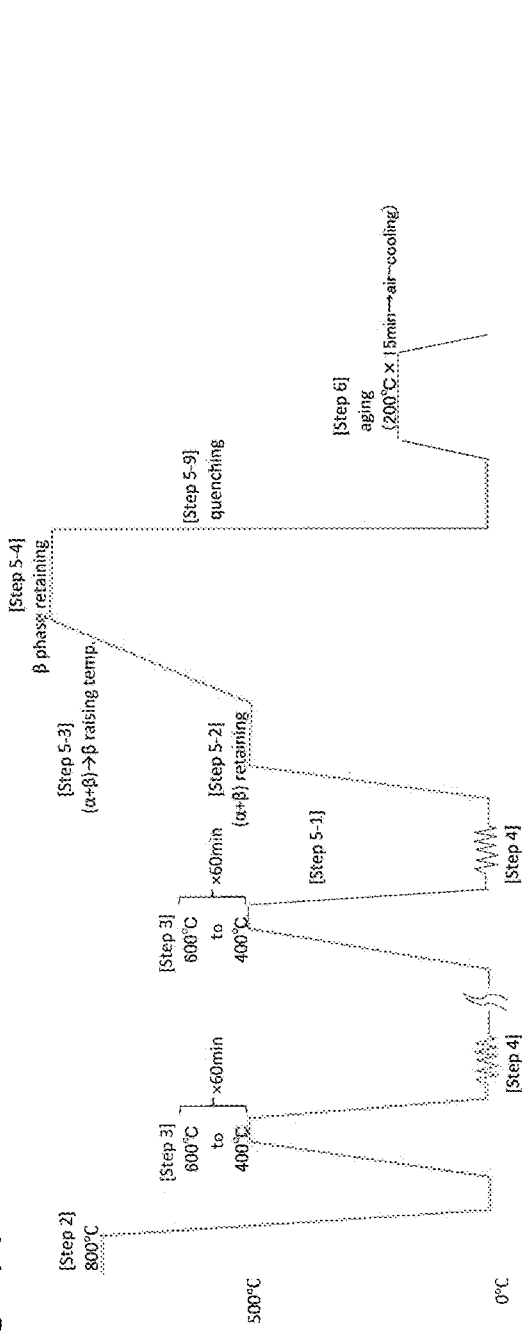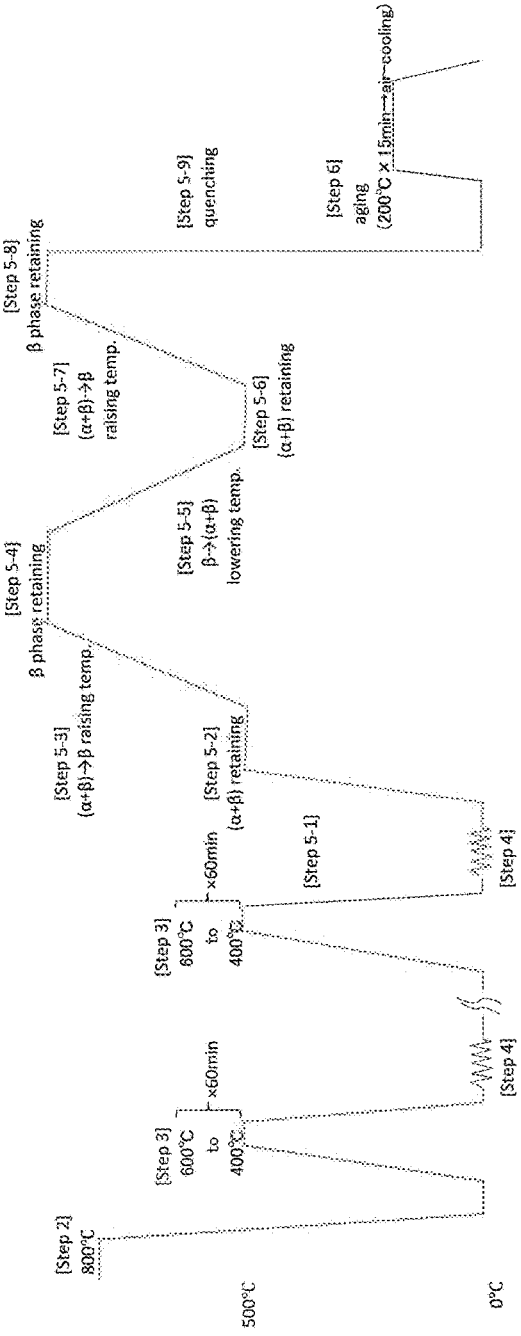
Fig. 2(a)
Fig. 2(b)

Fig. 4(a) Area ratio of brittle fracture 0% (100% ductile fracture)
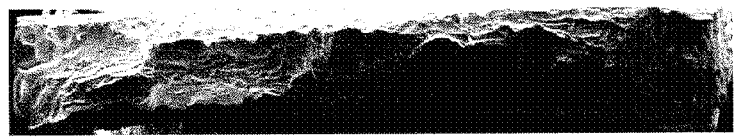
Fig. 4(b) Area ratio of brittle fracture 68.6%
Fig. 4( c ) Area ratio of brittle fracture 100%
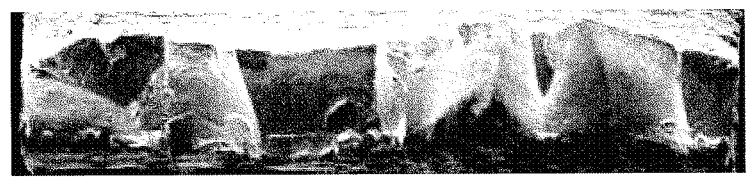
Fig. 4( d ) Fracture surface of Fig. 4(b) with meshes of 0.02 mm
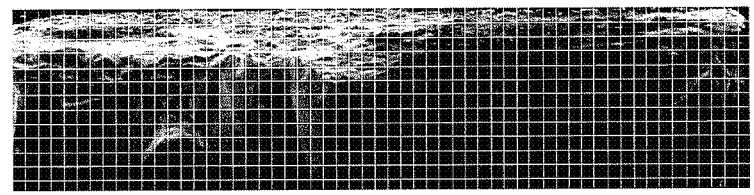

Distribution of crystalline characteristics

Grain boundary map

1mm

CSL chart

EBSD measured results of Example 10

Distribution of crystalline characteristics

Grain boundary map

CSL chart

EBSD measured results of Comparative Example 1

Fig. 6(a)   Example 13
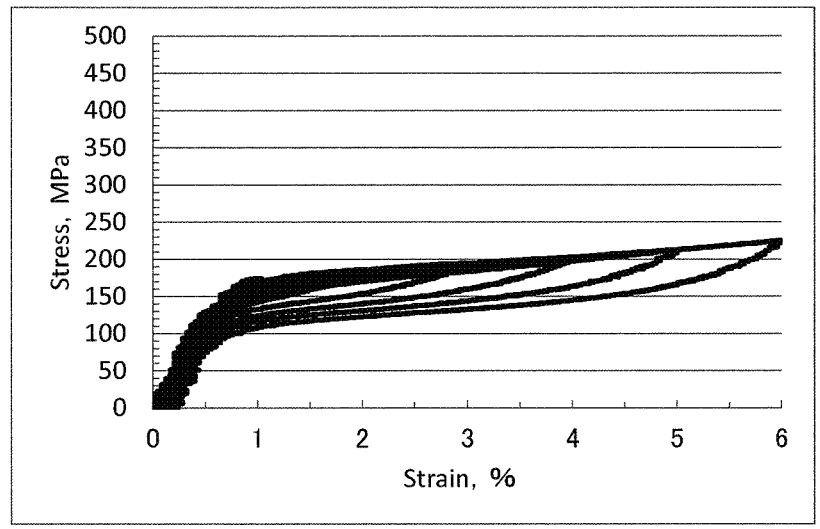
Fig. 6(b)   Comparative Example 1
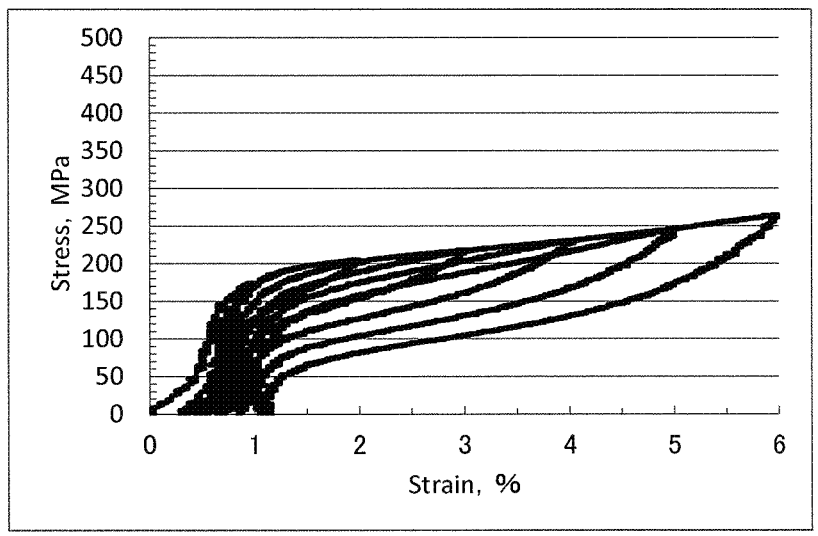

WROUGHT MATERIAL COMPRISING CU—AL—MN-BASED ALLOY EXCELLENT IN STRESS CORROSION RESISTANCE AND USE THEREOF

CROSS-REFERENCE TO RELATED APPLICATIONS

This application is a Continuation of PCT International Application No. PCT/JP2014/068400 filed on Jul. 10, 2014, which claims priority under 35 U.S.C. § 119 (a) to Japanese Patent Application No. 2013-148058 filed in Japan on Jul. 16, 2013. Each of the above applications is hereby expressly incorporated by reference, in its entirety, into the present application.

TECHNICAL FIELD

The present invention relates to a wrought material of a Cu—Al—Mn-based alloy controlling the coincidence grain boundary. Further, the present invention relates to a wrought material comprising a Cu—Al—Mn-based alloy excellent in stress corrosion resistance.

BACKGROUND ART

Shape memory alloys and superelastic alloys exhibit a remarkable shape memory effect and superelastic characteristics concomitantly to reverse transformation of the thermoelastic martensite transformation, and have excellent functions near the living environment temperature. Accordingly, these alloys have been put to practical use in various fields. Representative alloys of the shape memory alloys and superelastic alloys include TiNi alloys and copper (Cu)-based alloys. Copper-based shape memory alloys and superelastic alloys (hereinafter, those are simply referred to copper-based alloys) have characteristics inferior to those of TiNi alloys in terms of repetition characteristics, corrosion resistance, and the like. However, since the cost is inexpensive, there is a movement to extend the application range of copper-based alloys.

As an example of putting the copper-based alloy to practical use, the inventors of the present invention have proposed a correcting tool for ingrown toenail (so-called ingrown nail), which is comprised of a material obtained by subjecting to a shape-memory heat treatment on a cold-rolled sheet of a Cu—Al—Mn-based superelastic alloy, and which is excellent in durability of a nail-holding portion to repeated stress application (Patent Literature 1). The correcting tool for ingrown toenail described in Patent Literature 1 is intended to provide a correcting tool for ingrown toenail that is excellent in durability of a mounting portion (the nail-holding portion), in consideration of the use under the environment in which repeated deformation stress is applied. Further, in Patent Literature 1, regarding stress corrosion, prevention of occurrence of stress corrosion cracking in a stress corrosion test using an artificial perspiration (sweat) is tested and evaluated, in consideration of the case where a user goes about his/her daily life in a state where the correcting tool for ingrown toenail is mounted on the ingrown toenail.

Further, there is proposed austenitic stainless steel that is not a shape memory alloy or a superelastic alloy but that is intended to prevent occurrence of stress corrosion cracking (hereinafter, also referred to as SCC) by controlling a low sigma coincidence grain boundary frequency (Patent Literature 2).

CITATION LIST

Patent Literatures

Patent Literature 1: Japanese Patent No. 5144834
Patent Literature 2: JP-A-2011-168819 ("JP-A" means unexamined published Japanese patent application)

SUMMARY OF INVENTION

Technical Problem

The correcting tool for ingrown toenail described in Patent Literature 1 can enhance the prevention of occurrence of stress corrosion cracking. However, there is a demand for further enhancement or improvement in stress corrosion resistance including the prevention of occurrence of stress corrosion cracking in the correcting tool for ingrown toenail. In Patent Literature 1, a material for forming an alloy composition of Cu, Al, and Mn is melted and cast; then the thus-obtained ingot is subjected to descaling, hot forging, and hot rolling; on this hot-rolled sheet, cold rolling and intermediate annealing (600° C.×10 minutes) are repeatedly conducted at a working ratio of 40%; and after solutionizing treatment (900° C.×5 minutes) is conducted as shape-memory heat treatment is conducted, followed by aging (150° C.×20 minutes). Thus, a material is obtained, by subjecting the cold-rolled sheet as the Cu—Al—Mn-based superelastic alloy to shape-memory heat treatment. In Patent Literature 1, as the conditions for obtaining the superelastic characteristics effect, there is described that the Cu—Al—Mn-based alloy turns into the $\beta$ single phase at high temperature (two phase microstructure of $\beta+\alpha$ at low temperature) in the phase diagram of the Cu—Al—Mn-based alloy.

However, in Patent Literature 1, there is no description on the metal microstructure control of this Cu—Al—Mn-based superelastic alloy, particularly, the metal microstructure control in terms of grain boundary engineering. For this reason, in Patent Literature 1, there is absolutely no attention given to the control of coincidence grain boundary and the technique therefor, or what kind of influence would make on the control of the coincidence grain boundary on the stress corrosion resistance of the copper-based alloy.

Patent Literature 2 describes that grain boundary corrosion resistance and IGSCC resistance (SCC proceeding along the grain boundary, intergranular stress corrosion cracking) are improved by controlling coincidence grain boundary in austenitic stainless steel. In Patent Literature 2, austenitic stainless steel is subjected to cold rolling at a low rolling ratio of 2 to 5%, and then is subjected to heating in a short time period of 1 to 60 minutes at a heating temperature of 1,200 to 1,500 K, thereby for obtaining austenitic stainless steel in which an existence frequency of low $\Sigma$CSL grain boundary (coincidence grain boundary with a sigma value of 29 or less) is 75% or more. However, in Patent Literature 2, there is no description on a copper-based alloy, particularly, a copper-based shape memory alloy or superelastic alloy.

As described above, in the superelastic copper alloys that are obtained conventionally, the influence of the coincidence grain boundary control on superelastic characteristics is not studied, and there is no finding on enhancement in the stress corrosion resistance of the superelastic copper alloys.

The present invention is contemplated for providing: a Cu—Al—Mn-based alloy in which coincidence grain boundary is controlled; and a wrought material comprised of a Cu—Al—Mn-based alloy, which is excellent in stress corrosion resistance. Further, the present invention is contemplated for providing: a correcting tool for ingrown toenail, an orthosis for hallux valgus, a structural member, a spectacle frame, an actuator, or a connector, each of which is comprised of these materials.

Solution to Problem

The inventors of the present invention conducted a thorough investigation in order to solve the problems in the conventional art. As a result, the inventors of the present invention found that when the coincidence grain boundary of a Cu—Al—Mn-based alloy wrought material is properly controlled, it is possible to obtain a wrought material comprised of a Cu—Al—Mn-based alloy, which is excellent in stress corrosion resistance. The present invention was attained based on these findings.

The problems above can be solved by the following means:

(1) A wrought material comprised of a Cu—Al—Mn-based alloy, in which an existence frequency of a coincidence grain boundary with a Σ value of 3 or less is 35% or more but 75% or less, and which has a recrystallized microstructure substantially formed from a β single phase.

(2) A wrought material comprised of a Cu—Al—Mn-based alloy, in which an existence frequency of a coincidence grain boundary with a Σ value of 3 or less is 35% or more but 75% or less, in which a existence frequency of a coincidence grain boundary with a Σ value of 29 or less is 45% or more but 90% or less, and which has a recrystallized microstructure substantially formed from a β single phase.

(3) The wrought material comprised of a Cu—Al—Mn-based alloy described in the item (1) or (2), which is excellent in stress corrosion resistance.

(4) The wrought material comprised of a Cu—Al—Mn-based alloy described in any one of the items (1) to (3), wherein the wrought material is a sheet or a rod, wherein an existence ratio of grains having a grain size of (½) or more of a sheet thickness or a wire diameter of the wrought material in a cross section in a longitudinal direction is 80% or more of the cross-sectional area, and wherein an average grain size of the grains is in the range of 0.8 to 2.5 times more than the sheet thickness or the wire diameter of the wrought material.

(5) The wrought material comprised of a Cu—Al—Mn-based alloy described in any one of the items (1) to (4), which is excellent in superelastic characteristics.

(6) The wrought material comprised of a Cu—Al—Mn-based alloy in any one of the items (1) to (5), wherein the wrought material has an alloy composition comprising: 5 to 10 mass % of Al; 5 to 20 mass % of Mn; optionally 2 mass % or less of Ni; and optionally 0.001 to 10 mass % in total of at least one element selected from the group consisting of Co, Fe, Ti, V, Cr, Si, Nb, Mo, W, Sn, Mg, P, Be, Sb, Cd, As, Zr, Zn, and Ag, with the balance being Cu and unavoidable impurities.

(7) A correcting tool for ingrown toenail comprised of the wrought material of a Cu—Al—Mn-based alloy in any one of the items (1) to (6).

(8) An orthosis for hallux valgus comprised of the wrought material of a Cu—Al—Mn-based alloy in any one of the items (1) to (6).

(9) A structural member comprised of the wrought material of a Cu—Al—Mn-based alloy in any one of the items (1) to (6).

(10) A spectacle frame comprised of the wrought material of a Cu—Al—Mn-based alloy in any one of the items (1) to (6).

(11) An actuator comprised of the wrought material of a Cu—Al—Mn-based alloy in any one of the items (1) to (6).

(12) A connector comprised of the wrought material of a Cu—Al—Mn-based alloy in any one of the items (1) to (6).

The Cu—Al—Mn-based alloy wrought material of the present invention is preferably such that, as the superelastic characteristics, the residual strain after 6% strain loading is 1% or less.

Herein, the expression 'superelastic characteristics are excellent', the strain remaining when a predetermined loading strain or loading stress is applied thereto and then the load is eliminated, is referred to as residual strain, and it is desirably meant that this residual strain is small. It is more desirable as this residual strain is smaller. In the present invention, it is meant that the residual strain after 6% deformation is generally 1% or less, and preferably 0.5% or less.

In addition, the expression 'having a recrystallized microstructure substantially formed from a β single phase' means that the proportion occupied by the β phase in the recrystallized microstructure is generally 98% or more.

Advantageous Effects of Invention

The Cu—Al—Mn-based alloy wrought material of the present invention can be used in various applications where superelastic characteristics and stress corrosion resistance are required, and it is preferably applied, for example, to correcting tools for ingrown toenail (so-called correcting tools for ingrown nail). As other medical products, for example, applications are also expected in orthodontic wires, guide wires, stents, and orthoses for hallux valgus. Further, the Cu—Al—Mn-based alloy wrought material of the present invention is expected to be preferably in structural members, spectacle frames, actuators, connectors, as well as raw materials of antennas of mobile phones.

Other and further features and advantages of the invention will appear more fully from the following description, appropriately referring to the accompanying drawings.

BRIEF DESCRIPTION OF DRAWINGS

FIGS. 2(a) and 2(b) each illustrate a representative example of the preferable working and heating process chart. FIG. 2(a) is a chart illustrating an example of a working and heating process of quenching immediately after β phase retaining. FIG. 2(b) is a chart illustrating another example of the working and heating process of quenching, after retaining the β phase, cooling to the (α+β) phase temperature range, then raising temperature again to the β single-phase temperature range, and retaining this state.

FIG. 3(a) schematically illustrates the shape of a test piece. FIG. 3(b) schematically illustrates a state in which bending strain is applied to the test piece. FIG. 3(c) schematically illustrates a state in which the test piece is pulled until it is fractured (broken) after the bending strain is removed.

FIGS. 4(a) to 4(d) each are a SEM photograph showing a state in which the fracture surface is observed with a SEM after the stress corrosion test as illustrated in FIGS. 3(a) to 3(c). FIG. 4(a) is a SEM photograph of Example 1 in which 100% of the fracture surface was ductile fracture. FIG. 4(b) is a SEM photograph of Comparative Example 2 in which 68.6% of the fracture surface was brittle fracture. FIG. 4(c) is a SEM photograph of Comparative Example 1 in which 100% of the fracture surface was brittle fracture. FIG. 4(d) shows a fracture surface of the photograph of FIG. 4(b) with meshes.

FIGS. 6(a) and 6(b) each are a diagram illustrating a stress-strain curve (S-S curve) showing the measurement results of residual strain preformed in Examples. FIG. 6(a) shows a wrought material (a sheet, Example 13) obtained by repeating the process of intermediate annealing-cold-working four times at an intermediate annealing temperature of 600° C. and a cumulative cold-working ratio of 90%. FIG. 6(b) shows a wrought material (a sheet, Comparative Example 1) obtained by repeating the process of intermediate annealing-cold-working three times at an intermediate annealing temperature of 500° C. and a cumulative cold-working ratio of 80%.

MODE FOR CARRYING OUT THE INVENTION

Figure 1:
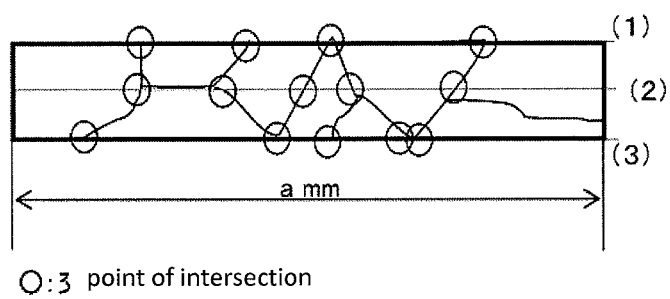
FIG. 1 is a schematic diagram illustrating a method for evaluating a grain size.

The Cu—Al—Mn-based alloy wrought material of the present invention stably exhibits good superelastic characteristics and is excellent in the stress corrosion resistance, by controlling crystalline characteristics (grain boundary characteristics) such that the existence frequency of the coincidence grain boundary with a Σ value of 3 or less is 35% or more.

The Cu—Al—Mn-based alloy according to the present invention indicates a material prepared by subjecting a Cu—Al—Mn-based alloy to plastic working. In the present invention, the Cu—Al—Mn-based alloy wrought material indicates a sheet, a bar, a rod, a tube, or the like, which is subjected to working, such as rolling, extracting, or drawing, and working in which the cross-sectional shape of a product that is obtained by heating after working has a constant cross-sectional shape, and which is not subjected to three-dimensional working, such as forging, in the cold-working stage as the final working stage of the product.

<Control of Coincidence Grain Boundary>

In the Cu—Al—Mn-based alloy wrought material of the present invention, the existence frequency of the coincidence grain boundary with a Σ value of 3 or less, that is, Σ1 to Σ3, is 35% or more but 75% or less, and this existence frequency is preferably 40% or more but 75% or less.

Further, in the Cu—Al—Mn-based alloy wrought material of the present invention, the existence frequency of the coincidence grain boundary with a Σ value of 29 or less, that is, Σ1 to Σ29, is preferably 45% or more but 90% or less, more preferably 50% or more but 90% or less, and this existence frequency is further preferably 55% or more but 90% or less.

(Coincidence Grain Boundary)

The coincidence grain boundary (also referred to as coincidence site lattice grain boundary or CSL grain boundary) refers to a grain boundary in which, when one of two adjacent groups of grains with a grain boundary interposed therebetween is rotated around a crystal axis of the adjacent one group of grains, a portion of the lattice points of one of the group of grains is also positioned at the lattice point of the other adjacent group of grains, for thereby constituting a sub-lattice that is commonly shared by both of the groups of grains. In the present invention, the coincidence grain boundary refers to a grain boundary with a Σ value of 29 or less which will be described below. In contrast to this, a grain boundary with a Σ value of more than 29 is referred to as a random grain boundary. As the coincidence grain boundary in the present invention, a coincidence grain boundary is preferred, which has a high existence frequency of the coincidence grain boundary with a low Σ value, such as a Σ value of 3 or less. The Σ value will be described later.

Regarding the property of grain boundaries, grain boundaries are roughly classified into the aforementioned coincidence grain boundary and the random grain boundary. Of these, the coincidence grain boundary has a low Σ value representing the crystalline characteristics, a high coincidence lattice (in which lattice points are periodically overlapped) density, and a low grain boundary energy. On the other hand, the random grain boundary has a low coincidence lattice point density, and has therefore high grain boundary energy.

(Crystalline Characteristic Σ Value)

If two crystalline lattices are virtually overlapped, some tens of percentages of the overall lattices in grains that are in a particular orientation relationship are coincident in orientation with each other, and these lattices themselves form a superlattice. A reciprocal of the ratio between the number of these coincidence lattice points and the number of crystal lattice points is referred to as a Σ value. Meanwhile, a grain having an inclination angle of less than 15° is considered to have a Σ value of 1.

(Measuring Method of Coincidence Grain Boundary by EBSD)

The state of the coincidence grain boundary is determined, by measuring and analyzing the crystalline characteristics of a copper alloy, that is, the crystalline orientation distribution (grain boundary map), using an EBSD (electron back-scattering diffraction pattern) analyzer.

First, the principle of an EBSD method will be generally described.

When a sample that is tilted at about 60 to 700 is irradiated with an electron beam, a diffracted electron beam is formed at each crystal plane in the region extending from the sample surface to a depth of about 50 nm or less. When this electron back-scattering diffraction is analyzed, information on the orientation analysis of a crystalline sample is obtained.

When the angle shift between the orientations of two adjacent grains is 2° or more, it is determined that there is a grain boundary, that is, the grains have different crystalline orientations.

In the present invention, whether the grain boundary is a coincidence grain boundary is analyzed by SEM-EBSD. A specific example of a measuring method thereof is as described in Examples, which are described below.

Figure 5:
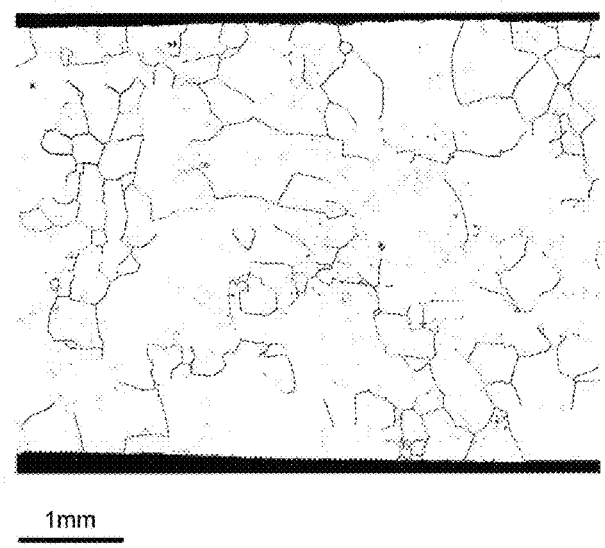
FIGS. 5(a1) to 5(b2) each are a diagram illustrating measurement results of coincidence grain boundary preformed in Examples. Regarding the results of Example 10, FIG. 5(a1) illustrates a grain boundary map, and FIG. 5(a2) illustrates a CSL chart. Regarding the results of Comparative Example 1, FIG. 5(b1) illustrates a grain boundary map, and FIG. 5(b2) illustrates a CSL chart.
Figure 5:
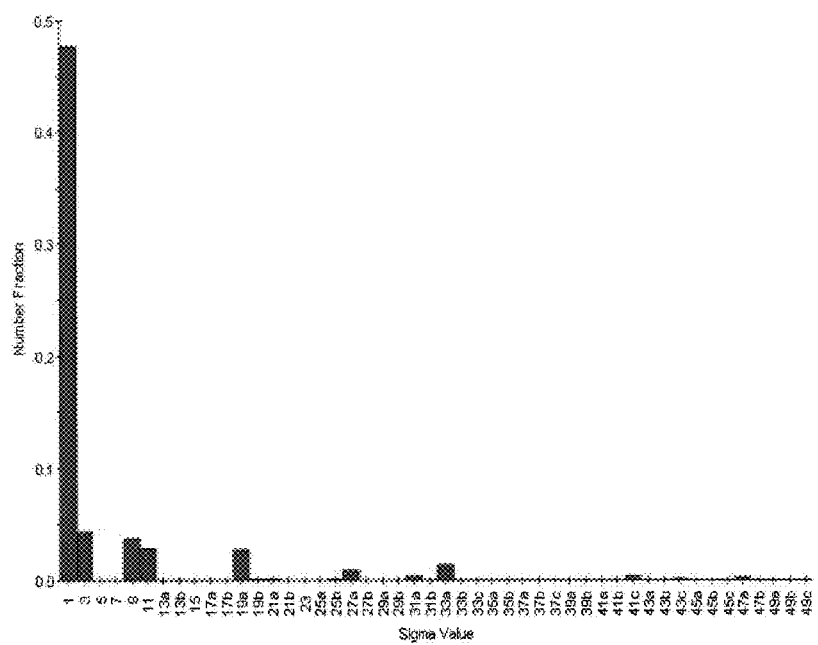
Figure 5:
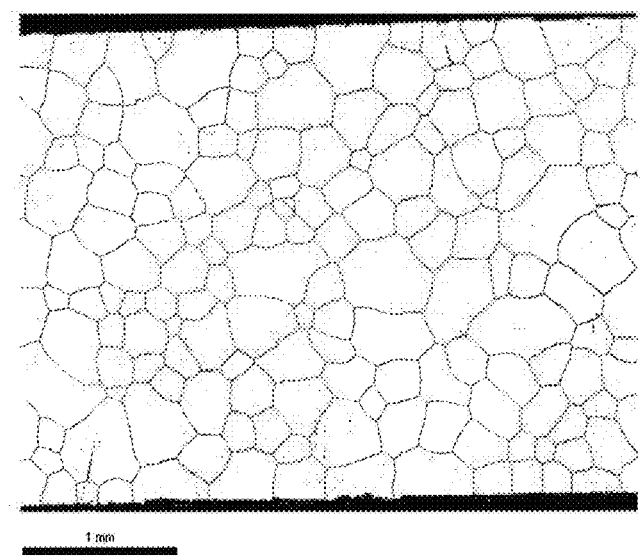
Figure 5:
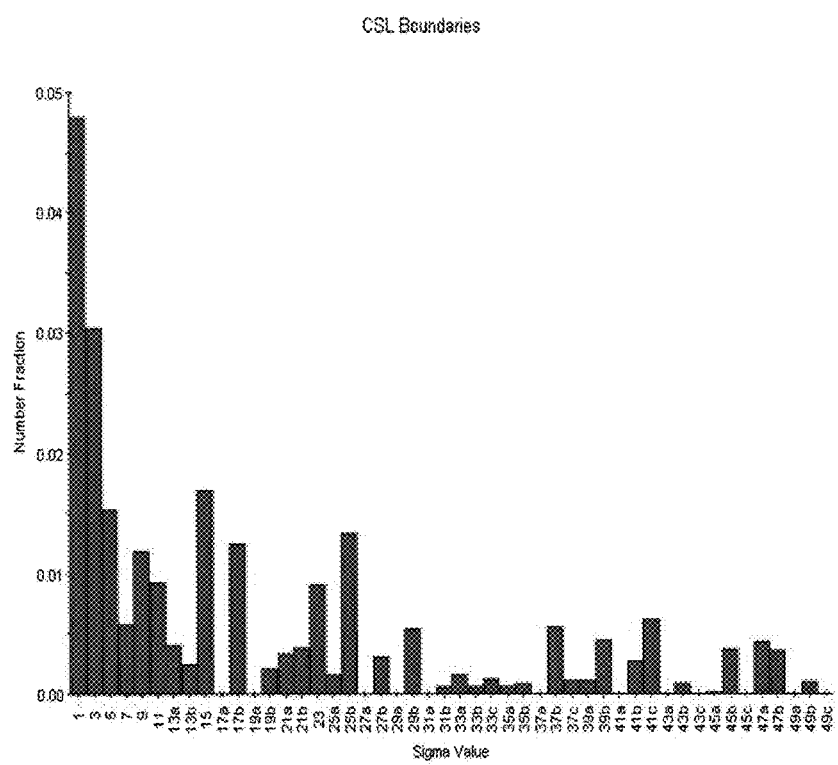

In a measurement of the coincidence grain boundary, a test piece for measuring coincidence grain boundary, which will be described later, is embedded in an electro-conductive resin, followed by subjecting to vibration-type buffing (polishing). The measurement is performed, by an EBSD method, in a measurement region of a size of about 400 μm×250 μm, under the condition of a scan step of 6 μm. Using OIM software (trade name, manufactured by TSL), the crystalline characteristics and the crystalline orientation obtained from all of the measured results are converted to a grain boundary map (for example, see FIGS. 5(a1) to 5(b2)). As will be described below, the Σ value is determined for each grain, and the existence frequency is determined for the coincidence grain boundary with a Σ value of 3 or less and the coincidence grain boundary with a Σ value of 29 or less, as the predetermined coincidence grain boundaries.

(Σ Value and Measuring Method Thereof)

When a rotation is made in the direction R about the point of origin O and the point P is designated as the coincidence lattice, the orientation at which the coincidence lattice appears, that is, the axis of rotation (h k l) is expressed as: $R^2=(h^2+k^2+l^2)$. When the coordinates of the coincidence lattice point P are designated as (x y z), and the angle of rotation is designated as θ (°), the angle of rotation is expressed as:

$$\theta=2\tan^{-1}(Ry/x).$$

Since the coincidence grain boundary is expressed as the Σ value, which is defined by the "reciprocal of the proportion of the unit cell volume of the coincidence lattice to the unit cell of grains," the coincidence grain boundary can be expressed as follows:

$$\Sigma=x^2+R^2y^2.$$

(Reference Literature) "Ceramic-Material Physics" edited by Yuichi IKUHARA, published by The Nikkan Kogyo Shimbun, Ltd., p. 83-86

(Frequency of Existence of Coincidence Grain Boundary)

In the present invention, the existence frequency of coincidence grain boundary (also referred to as the coincidence grain boundary frequency) indicates a ratio (percentage) of a predetermined coincidence grain boundary area to be focused to the overall grain boundary area. The existence frequency 1 means 100% (see the CSL charts of FIGS. 5(a1) to 5(b2)).

<Definitions of Grain Sizes and Controls Thereof>

In the Cu—Al—Mn-based copper alloys constituting the wrought material of the present invention, a little amount of the grains each having a small grain size may be present, but the most grains each have a large grain size.

Herein, the grains each having a large grain size means grains in which the grain size is (1/2) or more of the sheet thickness or the wire diameter in the sheet or the rod of the wrought material. Regarding the wrought material in the present invention, in any of the materials, all the existence ratios of the grains each having a grain size of (1/2) or more of the sheet thickness or the wire diameter of the wrought material in the cross section in the longitudinal direction are preferably 80% or more of the cross-sectional area of the cross section. Herein, the cross section in the longitudinal direction on which the measurement of the grain size is performed indicates the cross section in the longitudinal direction passing through the sheet thickness center of the sheet or the center of the circular cross section of the rod. Further, the average grain size of the grains in which the grain size in the cross section in the longitudinal direction of the wrought material passing through the center of the cross section of the wrought material is (1/2) or more of the sheet thickness or the wire diameter of the wrought material is preferably in the range of 0.8 to 2.5 times more than the sheet thickness or the wire diameter of the wrought material. More preferably, the average grain size is equal to or more than the sheet thickness or the wire diameter.

Further, in the case of a tube, the thickness of the tube wall is considered as the sheet thickness of the sheet, and the average grain size in this case is preferably the same as in the sheet.

Herein, microstructural characteristics are defined, by defining the average grain size of the grains each having a predetermined size or more.

Unlike the rod, the shape of the sheet is not a round-shaped cross section, and thus, has a low symmetric property. Thus, the standard of the grain size is a sheet thickness, not a sheet width. The reason is based on the fact that, after the grains penetrate through the sheet thickness or sheet width, the driving force of the growth of the grain boundary interface is lowered, and thus, the grains are increased in their sizes, but it is difficult to penetrate through the sheet width as well as the sheet thickness.

In the Cu—Al—Mn-based alloy rod and sheet of the present invention, the average grain size of the matrix (the base material) is to be the proper size. This is because in the Cu—Al—Mn-based alloys, when the average grain size is too small, the restriction between the grains is generated from the surrounding grains at the time of being deformed, and thus, the resistance to the deformation becomes larger, thereby deteriorating the superelastic characteristics. In the present invention, the upper limit of the average grain size is not particularly limited.

In the present invention, for the wrought material of the rod (wire) and sheet, by controlling the average grain size as described above, it is possible to stabilize the superelastic characteristics.

For the rod and sheet comprised of the Cu—Al—Mn-based alloy of the present invention, the grains in the predetermined size or more have the average grain size in the predetermined size or more. This is because the effect of the grains each having the size less than the predetermined size may be considered to be ignored, since the grain size of the grains each having the size that is the predetermined size or more is defined, the amount of the grains each having the size that is less than the predetermined size is conspicuously low as compared to the grains each having the size that is the predetermined size or more, and the effect to the superelastic characteristics is small.

<Metal Microstructure of Wrought Material and the State of Phase Thereof>

The Cu—Al—Mn-based alloy wrought material of the present invention is a material having a recrystallized microstructure.

Further, the Cu—Al—Mn-based alloy wrought material of the present invention is substantially composed of a β single phase. Herein, the expression 'being substantially composed of a β single phase' means that the existence ratio of a phase other than the β phase, for example, an α phase, is generally 2% or less. For example, a Cu-8.1 mass % Al-11.1 mass % Mn alloy is a β (BCC) single phase at 900° C., but is the two phases of an α (FCC) phase+the β phase at 700° C. or less.

<Composition of Cu—Al—Mn-Based Alloy Wrought Material>

The Cu—Al—Mn-based alloy wrought material of the present invention is formed of a copper alloy which has the β single phase at a high temperature, and a two-phase microstructure of β+α at a low temperature, and is formed of a copper-based alloy containing at least Al and Mn.

The Cu—Al—Mn-based alloy that forms the wrought material of the present invention has an alloy composition containing 5 to 10 mass % of Al and 5 to 20 mass % of Mn, with the balance being Cu and unavoidable impurities. If the content of elemental Al is too small, the β single phase cannot be formed, and if the content is too large, the resultant alloy becomes very brittle. The content of elemental Al may vary depending onto the content of elemental Mn, but a preferred content of elemental Al is 7 to 9 mass %. When the alloy contains elemental Mn, the range of existence of the β phase extends to a lower Al-content side, and cold workability is markedly enhanced, for thereby making the form-working property readily. If the amount of addition of elemental Mn is too small, satisfactory workability is not obtained, and the region of the β single phase cannot be formed. Also, if the amount of addition of elemental Mn is too large, sufficient shape recovery characteristics are not obtained. A preferred content of Mn is 8 to 13 mass %.

The Cu—Al—Mn-based alloy having the above-described alloy composition has high hot-workability and high cold-workability, and enables to obtain a working ratio of 20 to 90% or higher in cold-working, in combination with appropriate intermediate annealing. Thus, the wrought material of the present invention can be readily worked by forming into sheets (strips) and rods (wires), as well as fine wires, foils, pipes, and the like, each of which have been conventionally difficult to produce.

In addition to the essential alloying elements described above, the Cu—Al—Mn-based alloy that forms the wrought material of the present invention can further contain, as an optionally adding alloying element(s), at least one selected from the group consisting of Co, Fe, Ti, V, Cr, Si, Nb, Mo, W, Sn, Mg, P, Be, Sb, Cd, As, Zr, Zn, and Ag.

These elements exhibits the effects for enhancing the physical strength of the resultant Cu—Al—Mn-based alloy, while maintaining cold workability. The content in total of these elements is preferably 0.001 to 10 mass %, and particularly preferably 0.001 to 5 mass %. If the content of these elements is too large, the martensite transformation temperature is lowered, and the β single-phase microstructure becomes unstable. Regarding these optionally adding alloying elements, use can be made of the aforementioned elements that are generally used by being contained into copper-base alloys, for example, for the purpose of strengthening of copper alloys.

Co, Fe and Sn are elements that are effective for strengthening of the matrix microstructure. Co makes the grains coarse by forming CoAl; however, Co in an excess amount causes lowering of toughness of the alloy. A preferred content of Co is 0.001 to 2 mass %. A preferred content of Fe is 0.001 to 3 mass %. A preferred content of Sn is 0.001 to 1 mass %.

Ti is bonded to N and O, which are inhibitory elements, and forms oxynitride. A preferred content of Ti is 0.001 to 2 mass %. V, Nb, Mo and Zr have an effect of enhancing hardness, and enhance abrasion resistance. Further, since these elements are hardly solid-solubilized into the matrix, the elements precipitate as the β phase (bcc crystals), for thereby enhancing the physical strength. Preferred contents of V, Nb, Mo and Zr are respectively 0.001 to 1 mass %.

Cr is an element effective for retaining abrasion resistance and corrosion resistance. A preferred content of Cr is 0.001 to 2 mass %. Si has an effect of enhancing corrosion resistance. A preferred content of Si is 0.001 to 2 mass %. W is hardly solid-solubilized into the matrix, and thus has an effect of precipitation strengthening. A preferred content of W is 0.001 to 1 mass %.

Mg eliminates N and O, which are inhibitory elements, fixes S that is an inhibitory element as sulfide, and has an effect of enhancing hot workability or toughness. Addition of a large amount of Mg brings about grain boundary segregation, and causes embrittlement. A preferred content of Mg is 0.001 to 0.5 mass %. P acts as a de-oxidation agent, and has an effect of enhancing toughness. A preferred content of P is 0.01 to 0.5 mass %. Be, Sb, Cd, and As have an effect of strengthening the matrix microstructure. Preferred contents of Be, Sb, Cd and As are respectively 0.001 to 1 mass %.

Zn has an effect of raising the shape memory treatment temperature. A preferred content of Zn is 0.001 to 5 mass %. Ag has an effect of enhancing cold workability. A preferred content of Ag is 0.001 to 2 mass %.

The alloy composition of the Cu—Al—Mn-based alloy that forms the wrought material of the present invention may contain a Ni content of 2 mass % or less. More preferably, the Cu—Al—Mn-based alloy has a Ni content 0.15 mass % or less, and it is particularly preferable that the alloy does not contain Ni. It is because if the alloy contains Ni in a large amount, the quench-hardening property is deteriorated. Herein, the quench-hardening property (or quench-hardening sensitivity) indicates the relationship between the cooling speed in the quenching and the stability of microstructure in the quenching just before the quenching. In detail, when the cooling speed is slow at the time of the quenching, the phenomenon, in which an α phase is precipitated, and thus, superelastic characteristic is poor, is said that the quench-hardening property is sensitive. It is confirmed that since an α phase is started to be precipitated at higher temperature in the Ni-containing copper alloys, for example, a wire diameter becomes thick, and thus, the cooling time period becomes slightly longer, thereby making a quench-hardening property poor, and thereby, satisfactory superelastic characteristic may not be obtained.

<Method of Producing Cu—Al—Mn-Based Alloy Wrought Material>

A preferred production process and production conditions for obtaining the Cu—Al—Mn-based copper-based alloy wrought material of the present invention, will be described. For example, a production process such as described below may be mentioned. Further, a preferred example of the production process is illustrated in FIGS. 2(a) and 2(b).

In the overall production process, particularly, by heating to the (α+β) phase temperature range at the initial stage of the shape-memory heat treatment, and retaining the (α+β) phase temperature range once, and further by controlling the temperature-raising speed from the (α+β) phase temperature range to the β single-phase temperature range in the shape-memory heat treatment to be in a predetermined slow range (in the present patent application, this may also be referred to as slow-temperature raising), satisfactory superelastic characteristics are stably exerted, and a Cu—Al—Mn-based alloy wrought material with satisfactory stress corrosion resistance is obtained.

As a preferable example, the production process such as shown in FIG. 2(a), may be mentioned.

After melting and casting [Step 1] and hot-working [Step 2] of hot-rolling or hot-forging, intermediate annealing [Step 3] at 400° C. to 600° C. for 1 minute to 120 minutes, and cold-working [Step 4], in which the working ratio of the cold-rolling or cold-wire-drawing is in the range of 30% or more, are carried out in this order. Herein, the intermediate annealing [Step 3] and the cold-working [Step 4] may be performed once each in this order, or may be repeatedly performed twice or more in this order. Then, after shape-memory heat treatment [Step 5] is performed, aging [Step 6] is performed. Further, the intermediate annealing [Step 3] may also be omitted, depending on the cold-working degree.

The shape-memory heat treatment [Step 5] includes: heating [Step 5-1] of raising temperature from room temperature to the (α+β) phase temperature range by heating; [Step 5-2] of retaining the (α+β) phase temperature range; [Step 5-3] of heating from the (α+β) phase temperature range to the β single-phase temperature range at a predetermined slow temperature-raising speed (slow-temperature raising); [Step 5-4] of retaining the β single-phase temperature range (this corresponds to solutionizing); and [Step 5-9] of quenching from the β single-phase temperature range. In the present invention, the retaining of [Step 5-2] is performed, and thus the existence frequency of the coincidence grain boundary can be increased by heating from the (α+β) phase temperature range to the β single-phase temperature range at a predetermined slow temperature-raising speed.

Herein, in the heating [Step 5-3], the temperature-raising speed (slow-temperature raising described above) at which the heating is performed from the (α+β) phase temperature range to the β single-phase temperature range is generally 20° C./min or less, preferably 10° C./min or less, and further preferably 5° C./min or less. The lower limit thereof is not particularly limited, but is generally set to 1° C./min or more. The (α+β) phase temperature range varies depending on the composition of an alloy, but is 400° C. to 700° C. In addition, the β single-phase temperature range varies depending on the composition of an alloy, but is generally 700° C. to 950° C., and preferably 800° C. to 900° C.

Further, for the quenching [Step 5-9], a so-called quenching is carried out. For example, such a quenching may be performed by the water-cooling, in which the Cu—Al—Mn-based alloys wrought material subjected to the shape-memory heat treatment are put into the cooling water.

After the heating [Step 5], it is preferable to perform the aging-heating [Step 6] at 80° C. to 250° C. for 5 minutes to 60 minutes. If the aging temperature is too low, the β phase becomes unstable, and if the alloy is left to stand at room temperature, the martensite transformation temperature may change in some cases. On the contrary, if the aging temperature is too high, precipitation of the α phase occurs, and thus the shape memory characteristics or superelastic characteristics tend to be lowered conspicuously.

A desired coincidence grain boundary can be more preferably achieved, by repeatedly subjecting to the intermediate annealing [Step 3] and the cold-working [Step 4]. The number of repetitions of the intermediate annealing [Step 3] and the cold-working [Step 4] is preferably twice or more.

When the intermediate annealing [Step 3] and the cold-working [Step 4] are repeatedly performed, as the working ratio in the cold-working [Step 4], the working ratio throughout the cumulative working (hereinafter, also referred to as the cumulative working ratio) is desirably set to be a predetermined working ratio of 30% or more.

Preferred conditions for the steps are as follows.

The intermediate annealing [Step 3] is performed at 400° C. to 600° C. for 1 minute to 120 minutes. It is preferable that this intermediate annealing temperature be set to a lower temperature within this range. The intermediate annealing temperature is preferably set to 450° C. to 550° C., and particularly preferably 450° C. to 500° C. The annealing time period is preferably 1 minute to 120 minutes, and even if the influence of the sample size is considered, an annealing time period of 120 minutes is sufficient for a round rod with a diameter of φ 20 mm. The intermediate annealing [Step 3] may be omitted as described above.

For the cold-working [Step 4], it is preferable to carry out the step at a working ratio of 30% or higher, more preferably 40% or higher, further preferably from 50 to 95%, and particularly preferably from 60 to 90%. Herein, the working ratio is a value defined by formula:

Working ratio (%)=$\{(A_1-A_2)/A_1\}\times 100$ wherein $A_1$ represents the cross-sectional area (mm$^2$) obtained before the cold-working of cold-rolling or cold-wire-drawing; and $A_2$ represents the cross-sectional area (mm$^2$) obtained after the cold-working of cold-rolling or cold-wire-drawing.

If the intermediate annealing [Step 3] and the cold-working [Step 4] are repeatedly performed, it is sufficient that the cumulative working ratio throughout the overall cold-working [Step 4] is within the range described above.

When the heating is performed in the heating [Step 5-1], the temperature-raising speed at this time is not particularly limited, as long as temperature reaches the temperature range of the [Step 5-2] retaining in the (α+β) phase temperature range, by raising the temperature. In the retaining [Step 5-2], the retaining time period in the (α+β) phase temperature range is preferably 20 minutes to 120 minutes, and further preferably 30 minutes to 120 minutes. In this way, it is necessary to perform the retaining in the (α+β) phase temperature range and sufficiently lengthen the retaining time period. Thus, the retaining time period is lengthened, and as a result, the formation of the coincidence grain boundary can be accelerated.

The temperature-raising speed when the heating is performed in the heating [Step 5-3] at a slow-temperature raising is generally 20° C./min or less, preferably 10° C./min or less, and further preferably 5° C./min or less. The lower limit thereof is not particularly limited, but is generally set to 1° C./min or more. When this temperature-raising speed is set to a predetermined slow speed (slow-temperature raising), the coincidence grain boundary can be stably formed.

In the retaining [Step 5-4], the retaining time period in the β single-phase temperature range is preferably 2 minutes to 120 minutes, and further preferably 10 minutes to 120 minutes.

The cooling speed at the time of the quenching [Step 5-9] is generally 30° C./sec or more, preferably 100° C./sec or more, and further preferably 1,000° C./sec or more.

The aging [Step 6] is preferably performed at generally a temperature lower than 300° C. and preferably at 80° C. to 250° C. for 5 minutes to 60 minutes. After the aging [Step 6], cooling may be performed by general air-cooling.

As another preferable example, the production process such as shown in FIG. 2(b), may be mentioned.

The production process shown in FIG. 2(b) is the same as the production process shown in FIG. 2(a) in that the melting and casting [Step 1], the hot-working [Step 2], the intermediate annealing [Step 3] and the cold-working [Step 4](these two steps are repeated once each in this order or twice or more in this order), and the aging [Step 6] finally performed, except that the shape-memory heat treatment [Step 5] is different from that shown in FIG. 2(a) on the point described below. In addition, the preferred working and heating conditions are the same. The intermediate annealing [Step 3] may be omitted as described above.

The shape-memory heat treatment [Step 5] in the production process shown in FIG. 2(b) is the same as the production process shown in FIG. 2(a), which includes: the heating [Step 5-1] of raising temperature from room temperature to the (α+β) phase temperature range by heating; [Step 5-2] of retaining the (α+β) phase temperature range; [Step 5-3] of heating from the (α+β) phase temperature range to the β single-phase temperature range at a predetermined slow temperature-raising speed (slow-temperature raising); [Step 5-4] of retaining the β single-phase temperature range; and [Step 5-9] of quenching from the β single-phase temperature range finally performed. In addition, the preferred working and heating conditions are also the same. However, the steps after the retaining [Step 5-4] to the quenching [Step 5-9] are different from those in the production process shown in FIG. 2(a).

That is, after the retaining [Step 5-4], cooling [Step 5-5] in which the temperature is lowered from the β single-phase temperature range to the (α+β) phase temperature range by cooling, [Step 5-6] of retaining the (α+β) phase temperature range, [Step 5-7] of heating from the (α+β) phase temperature range to the β single-phase temperature range at a predetermined slow temperature-raising speed (slow-temperature raising), and [Step 5-8] of retaining the β single-phase temperature range are performed, and then the quenching [Step 5-9] is performed.

In the cooling [Step 5-5], the temperature-lowering speed at the time of cooling from the β single-phase temperature range to the (α+β) phase temperature range (which will be referred to, herein, 'slow-temperature-lowering' or 'slow-cooling') is generally 20° C./minute or less, preferably 10° C./minute or less, and more preferably 5° C./minute or less. The lower limit value of this speed is not particularly limited, but is generally 1° C./minute or more.

In the heating [Step 5-7], the temperature-raising speed at which the heating is performed from the (α+β) phase temperature range to the β single-phase temperature range is preferably set to the same slow-temperature raising as described above, and the preferred conditions thereof are also the same.

In the example of this production process, the slow-cooling in the cooling [Step 5-5] and the slow-temperature raising in the heating [Step 5-7] make grains coarse. For this reason, it is considered that the coincidence grain boundary and the superelastic characteristics can be preferably controlled.

The preferred conditions in each step of [Step 5-5] to [Step 5-8] are as follows.

The slow-cooling speed at the time of the cooling [Step 5-5] is generally 20° C./min or less, preferably 10° C./min or less, and further preferably 5° C./min or less. The lower limit thereof is not particularly limited, but is generally set to 1° C./min or more.

In the retaining [Step 5-6], the retaining time period in the (α+β) phase temperature range is preferably 5 minutes to 120 minutes, and further preferably 30 minutes to 120 minutes.

The temperature-raising speed in the heating [Step 5-7] is generally 20° C./min or less, preferably 10° C./min or less, and further preferably 5° C./min or less. The lower limit thereof is not particularly limited, but is generally set to 1° C./min or more.

In the retaining [Step 5-8], the retaining time period in the β single-phase temperature range is preferably 1 minute to 120 minutes, and further preferably 30 minutes to 120 minutes.

Further, the treatment temperatures and treatment time periods (retaining time periods) in the respective heating as shown in the figures are the representative examples utilized in the following Examples, respectively. The preferred production process as applied to the present invention is not limited to those.

<Physical Properties>

The Cu—Al—Mn-based alloy wrought material of the present invention has the following physical properties.

Regarding the superelastic characteristics, the residual strain after 6% deformation is generally 1.0% or less, and preferably 0.5% or less.

<Shape and Size of Wrought Material>

There are also no particular limitations on the shape of the Cu—Al—Mn-based alloy wrought material of the present invention, and, for example, any shape of sheet, wire (rod), and the like may be taken. There are also no particular limitations on the sizes of the Cu—Al—Mn-based alloy wrought material of the present invention. For example, the sheet may have the thickness of 0.1 mm to 15 mm. Further, in the case of the wire (rod), the diameter thereof may also be employed, for example, 0.1 mm to 50 mm. The diameter of the wire (rod) may be the size of 8 mm to 16 mm depending on the use thereof. Further, the wrought material of the present invention may have the shape of a tube having a tube wall and a hollow shape.

<Products for Application>

Since the Cu—Al—Mn-based alloy wrought material of the present invention is excellent in stress corrosion resistance, it can be preferably utilized, for example, in correcting tools for ingrown toenail, orthoses for hallux valgus, structural members, spectacle frames, actuators, connectors, and the like. Thus, there can be provide correcting tools for ingrown toenail, orthoses for hallux valgus, structural members, spectacle frames, actuators, connectors, and the like, each comprised of the Cu—Al—Mn-based alloy wrought material of the present invention.

EXAMPLES

The present invention will be described in more detail based on examples given below, but the invention is not meant to be limited by these.

Example 1

Samples (specimen) of sheets and rods (wires) were produced under the following conditions.

For obtaining the copper alloys that give the alloy compositions as indicated in Table 1-1 and Table 1-2, pure copper, pure Al, pure Mn, and materials of other optionally adding alloying elements were subjected, respectively, to melting in a high-frequency induction furnace.

For the production method of the sheets, the copper alloys thus melted were cooled, to obtain ingots with diameter of 80 mm×length of 300 mm. The thus-obtained ingots were subjected to hot forging at 800° C., to obtain thick sheets of the cross section with sheet thickness about 18 mm. These sheets were subjected to hot rolling at a pass schedule for five passes of the sheet thicknesses 18 mm→14 mm→10 mm→6 mm→4 mm→2 mm, to yield sheets with a sheet thickness of 2 mm ([Step 2] of FIG. 2(a)). Thereafter, thin sheets with a sheet thickness of 0.2 mm to 1.6 mm were produced by repeatedly subjecting to the intermediate annealing and the cold rolling at least once or more, under the conditions shown in Table 2-1, respectively, according to the each working and heating process shown in [Step 3] and [Step 4] of FIG. 2(a).

Herein, the reduction (cumulative working ratio) at the time of rolling the sheets with a sheet thickness of 2 mm to a predetermined sheet thickness that is a sheet thickness of 0.2 mm to 1.6 mm, was 20% to 90%, and the reduction of the cold rolling was determined to be in this range. As shown in Table 2-1, in Example 3, the intermediate annealing [Step 3] was omitted and not performed.

Samples of the sheets were also produced under the production conditions in which the working and heating process of [Step 3] and [Step 4] before the shape memory heat treatment of the sheets, which were performed as shown in Tables 2-1 and 2-2, at an annealing temperature of 500° C. and a cumulative working ratio of the cold rolling of 80%, were set as the 'standard conditions' (standard step), the annealing temperature was changed from 350° C. to 700° C., and the cumulative working ratio of the cold rolling was changed to a predetermined range of 20% to 90%.

For the production method of the rods (wires), the copper alloys thus melted were cooled, to obtain ingots with diameter of 80 mm×length of 300 mm. The thus-obtained ingots were subjected to hot forging, to obtain round rods with diameter 20 mm. The round rods were further subjected to, as necessary: (1) hot forging to diameter 18 mm; or (2) hot-wire-drawing with a pass schedule of diameter 18 mm→14 mm→10 mm→7 mm→5 mm→4 mm→3 mm→2 mm, by use of a tandem-type rod/wire-drawing machine, thereby for obtaining rods with rod diameter 2.0 mm (φ 2.0 mm) ([Step 2] of FIG. 2(a)). Thereafter, wires each with wire diameter 1.79 mm, 1.68 mm, 1.26 mm, 0.88 mm, or 0.63 mm were obtained by repeatedly subjecting to the intermediate annealing and the cold rolling at least once or more, under the conditions shown in Table 2-3, respectively, according to the each working and heating process shown in [Step 3] and [Step 4] of FIG. 2(a), so as to apply approximately the same reduction of 20% to 90% as in the cases of the above sheets.

Samples of the rods (wires) were also produced under the production conditions in which the working and heating process of [Step 3] and [Step 4] before the shape memory heat treatment of the rods (wires), which were performed as shown in Tables 2-3 and 2-4, at an annealing temperature of 500° C. and a cumulative working ratio of the cold rolling of 80%, were set as the 'standard conditions' (standard step), the annealing temperature was changed from 350° C. to 700° C., and the cumulative working ratio of the cold rolling was changed to a predetermined range of 20% to 90%.

In the sheets, small pieces having a size of 150 mm in length×20 mm in width were cut out in parallel to the rolling direction from each of the thin sheets thus obtained, and in the rods (wires), small pieces having a size of 150 mm in length were cut out from each of the rods (wires) thus obtained. For the sheets, each of 12 cut test pieces of each of these small pieces was subjected to the shape-memory heat treatment according to the working and heating process shown in [Step 5] of FIG. 2(a) under each working and heating condition, and then subjected to quenching by water cooling, thereby for obtaining each sample of a β (BCC) single phase of the thin sheets. Although described later, samples of the thin sheets are subjected to working for the stress corrosion cracking property test such that the width of 20 mm becomes the width of 1.5 mm. For the rods (wires), each of 60 cut test pieces of each of these small pieces was subjected to the shape-memory heat treatment according to the working and heating process shown in [Step 5] of FIG. 2(a) under each working and heating condition, and then subjected to quenching by water cooling, thereby for obtaining each sample of a β (BCC) single phase of the rods (wires). The (α+β) phase temperature range was set to 500° C. and the 1 single-phase temperature range was set to 850° C. Each sample was subjected to the aging-heating of [Step 6] of FIG. 2(a) at 200° C. for 15 minutes, for thereby obtaining desired thin sheets or rods (wires).

FIG. 2(a) is a chart illustrating a representative process, and the process was performed in such a manner that the temperature and time period of the intermediate annealing, the working ratio of the cold-working (cumulative working ratio if the cold-working was performed in plural times), the retaining time period in the (α+β) phase temperature range, the temperature-raising speed from the (α+β) phase temperature range to the β single-phase temperature range, and the retaining time period in the β single-phase temperature range were changed as shown in Table 2-1 and Table 2-3. Herein, the cold rolling or wire drawing was performed at a working ratio described in Table 2-1 and Table 2-3 (unless otherwise specified, at a cumulative working ratio of the standard condition described in each table). Further, before each cold rolling or wire drawing, the intermediate annealing was performed at an intermediate annealing temperature described in Table 2-1 and Table 2-3 (unless otherwise specified, at an annealing temperature of the standard condition described in each table).

Hereinafter, an example of the working process in the case where the intermediate annealing and the cold rolling are performed in plural times to obtain thin sheets, is illustrated together with the sheet thickness and the working ratio. For the intermediate annealing conditions, the annealing temperature and the annealing time period in each time are the same, and the conditions are set as described above.

[Example of Working Process of Sheet Test Piece]

The tensile test, the test for the stress corrosion cracking property, and the coincidence grain boundary analysis by EBSD were performed in such a manner that sheets adjusted to have a predetermined length was subjected to the aging as shown in [Step 6] of FIG. 2(a). Thereafter, five types of sheets having a sheet thickness of 1.6 mm, 1.4 mm, 0.8 mm, 0.4 mm, or 0.2 mm, respectively, were subjected to mechanical working and polishing such that the sheet thickness was adjusted to a constant sheet thickness of 0.2 mm, thereby for obtaining test pieces with sheet thickness 0.2 mm×width 20 mm×length 150 mm. In the test for the stress corrosion cracking property, use was made of test pieces obtained by cutting the above test pieces to width 1.5 mm.

Since the measurement of the grain size was affected by the cold-working ratio, test pieces having a sheet thickness of 1.6 mm, 1.4 mm, 0.8 mm, 0.4 mm, or 0.2 mm×a width of 20 mm×a length of 150 mm that are materials subjected to the aging were used without any changes.

[Example of Working Process of Rod (Wire) Test Piece]

The tensile test, the test for the stress corrosion cracking property, and the coincidence grain boundary analysis by EBSD were performed in such a manner that sheets adjusted to have a predetermined length was subjected to the aging as shown in [Step 6] of FIG. 2(a). Thereafter, five types of rods (wires) having a wire diameter of 1.79 mm, 1.68 mm, 1.26 mm, 0.88 mm, or 0.63 mm, respectively, were subjected to centerless polishing and then buffing such that the diameter was adjusted to 0.60 mm, thereby for obtaining test pieces with a wire diameter of 0.6 mm×a length of 150 mm.

Since the measurement of the grain size was affected by the cold-working ratio, test pieces having a wire diameter of 1.79 mm, 1.68 mm, 1.26 mm, 0.88 mm, or 0.63 mm×a length of 150 mm that are materials subjected to the aging were used without any changes.

An optical microscope was used for microstructure observation, and EBSD was used for coincidence grain boundary analysis. In the coincidence grain boundary analysis and the grain size measurement, each one test piece (N=1) was cut out from each one specimen and then tested.

For evaluating the superelastic characteristics, the stress loading-unloading by a tensile test was carried out, to obtain a stress-strain curve (S-S curve), thereby for determining and evaluating a residual strain. For the tensile test, five test pieces (N=5) were cut out from one specimen, to test. In the following test results, the residual strain was the average value obtained from those five values.

Separately, Comparative Examples (sheets) described in Table 2-2 were obtained according to the process chart shown in FIG. 2(a) in the same manner as the sheets of Examples, except that alloys shown Table 1-1 and Table 1-2 were changed as shown in Table 2-2, and that the temperature and time period of the intermediate annealing, the working ratio of the cold-working (cumulative working ratio if the cold-working was performed in plural times), the retaining time period in the (α+β) phase temperature range, the temperature-raising speed from the (α+β) phase temperature range to the β single-phase temperature range, and the retaining time period in the β single-phase temperature range were changed as shown in Table 2-2. Herein, the cold rolling was performed at a working ratio described in Table 2-2 (unless otherwise specified, at a cumulative working ratio of the standard condition described in each table). Further, before each cold rolling, the intermediate annealing was performed at an intermediate annealing temperature described in Table 2-2 (unless otherwise specified, at an annealing temperature of the standard condition described in each table).

Comparative Examples (rods (wires)) described in Table 2-4 were obtained according to the process chart shown in FIG. 2(a) in the same manner as the rods (wires) of Examples, except that alloys shown Table 1-1 and Table 1-2 were changed as shown in Table 2-4, and that the temperature and time period of the intermediate annealing, the working ratio of the cold-working (cumulative working ratio if the cold-working was performed in plural times), the retaining time period in the (α+β) phase temperature range, the temperature-raising speed from the (α+β) phase temperature range to the β single-phase temperature range, and the retaining time period in the β single-phase temperature range were changed as shown in Table 2-4. Herein, the cold-wire-drawing was performed at a working ratio described in Table 2-4 (unless otherwise specified, at a cumulative working ratio of the standard condition described in each table). Further, before each cold-wire-drawing, the intermediate annealing was performed at an intermediate annealing temperature described in Table 2-4 (unless otherwise specified, at an annealing temperature of the standard condition described in each table).

Various characteristics were tested and evaluated for sheets and rods (wires) composed of the thus-obtained Cu—Al—Mn-based alloy.

The methods for tests and evaluations are described in detail below.

Further, in Table 2-1 to Table 2-4, the results of the tests and the evaluations of Examples according to the present invention and Comparative Examples (sheets and rods (wires)) are collectively shown, together with the kinds of alloys and process conditions.

a. Evaluation of Coincidence Grain Boundary

The central portion of the respective test piece was cut to a size of 25 mm, the cut piece was embedded in an electro-conductive resin, and subjected to buffing and then chemical polishing to finish. The analysis was performed by an EBSD method, in an analysis region having a size of about 400 μm×250 μm, under the conditions of a scan step of 6 μm. Using OIM software (trade name, manufactured by TSL), the crystalline characteristics and the crystalline orientation obtained from all of the analytic results were converted to a grain boundary map (for example, see FIGS. 5(a1) to 5(b2)).

The Σ value was determined for each grain, a ratio of a predetermined coincidence grain boundary area to the overall grain boundary area was calculated for the coincidence grain boundary with a Σ value of 3 or less and the coincidence grain boundary with a Σ value of 29 or less, and then the obtained ratio (%) was considered as an existence frequency. The results of the existence frequency evaluation of the coincidence grain boundaries of Examples according to the present invention and Comparative Examples (sheets and rods (wires)) are shown in Table 2-1 to Table 2-4.

b. Stress Corrosion Resistance

The stress corrosion resistance was evaluated by the following test.

Figure 3A:
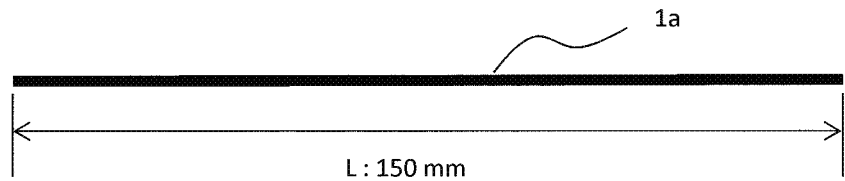
FIGS. 3(a) to 3(c) each are a schematic diagram illustrating a method for a stress corrosion test performed in Examples.

The schematic diagram of a test piece 1a is shown in FIG. 3(a). For the test pieces of the sheets, the test pieces having a size of a thickness (T) of 0.2 mm×a width (W) of 1.5 mm×a length (L) of 150 mm were cut out as described above, and also for test pieces of the rods (wires), the test pieces having a size of a wire diameter (φ) of 0.6 mm×a length (L) of 150 mm were used.

Figure 3B:
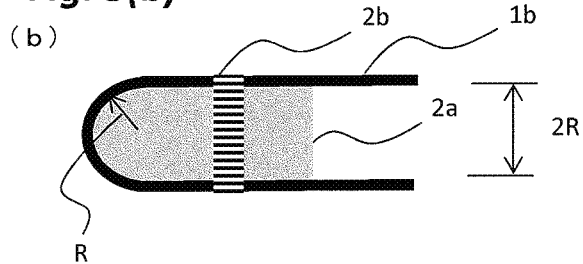

A plastic sheet 2a, in which the bending strain (loading strain) was properly adjusted to be 2% and one end had a radius R and had a sheet thickness of 2R, was crept on the test piece of the sheet and rod (wire), and then the test piece was bound with a plastic band 2b so as to be bent in a U shape (FIG. 3(b)). In the drawing, reference numeral 1b indicates the test piece bent in a U shape.

Figure 3C:
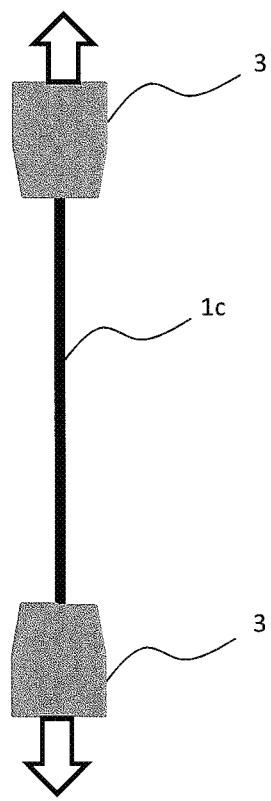

The test piece in this state was retained under the artificial perspiration (artificial sweat) (lactic acid 5%+sodium chloride 10%+water) as the humid environment defined by JIS B7285. The retaining temperature was set to 55° C. and the retaining time period was set to 72 hr. The stress corrosion resistance test was performed on 50 test pieces (N=50) for each specimen. After completion of the humid environment retaining, both ends of the test piece was gripped with grippers 3 and 3, and then the test piece was pulled until it was fractured (broken) (FIG. 3(c)). In the drawing, reference numeral ic indicates the test piece extended from the U shape. The fracture surface of the test piece after fracturing was observed with a scanning electron microscope (SEM) at a magnification of 60 folds (×60). Based on the results of the fracture surface observation, the stress corrosion resistance was evaluated according to the following criteria of three grades.

Stress corrosion resistance "excellent" (in the tables, A): The area ratio of brittle fracture is 3% or less.

Stress corrosion resistance "good" (in the tables, B): The area ratio of brittle fracture is more than 3% but less than 10%.

Stress corrosion resistance "poor" (in the tables, C): The area ratio of brittle fracture is 10% or more.

According to the evaluation criteria, the results of evaluation on the stress corrosion resistance of Examples according to the present invention and Comparative Examples (sheets and rods (wires)) are shown in Table 2-1 to Table 2-4.

The grain boundary fracture (brittle fracture) and the ductile fracture were distinguished by the aspect of the grain boundary, the existence of dimples, and the like, obtained from the SEM observation.

As an example of the fracture surface, in order to show the transition state from the ductile fracture surface to the brittle fracture surface, the results obtained by observing three types of fracture surfaces having a different area ratio of the brittle fracture surface are shown in FIGS. 4(a) to 4(c).

FIG. 4(a) shows a SEM photograph of the fracture surface obtained from Example 1 in which the brittle fracture area ratio was 0% (evaluation result of A in the tables), FIG. 4(b) shows a SEM photograph of the fracture surface obtained from Comparative Example 2 in which the brittle fracture area ratio was 68.6% (evaluation result of C in the tables), and FIG. 4(c) shows a SEM photograph of the fracture surface obtained from Comparative Example 1 in which the brittle fracture area ratio was 100% (evaluation result of C in the tables).

c. Method of Obtaining Area Ratio of Brittle Fracture Surface

The specific method of measuring the area ratio of the brittle fracture will be described by means of Comparative Example 2. First, the fracture surface photograph obtained by observing and photographing the fracture surface subjected to the stress corrosion resistance test with scanning electron microscope (SEM) is shown with 0.02-mm meshes vertically and horizontally. The number of meshes in the brittle fracture surface (designated as a), the number of meshes in the ductile fracture surface (designated as b), and the number of meshes in which both the brittle fracture surface and the ductile fracture surface exist (designated as c) are counted. A mesh in which both the fracture surface and the background exist is counted as one mesh regardless of brittle and ductile fractures, and this counted value is added to the mesh number c. The area ratio of the brittle fracture (designated as d) from the counted numbers of respective meshes is calculated by the following equation.

$$d=(a+c\times 0.5)/(a+b+c)$$

FIG. 4(d) shows a fracture surface of the photograph of FIG. 4(b) with meshes.

The mesh number a of the brittle fracture was 214, the mesh number b of the ductile fracture was 86, and the mesh number c in which both the brittle fracture surface and the ductile fracture surface exist was 45.

Therefore, the area ratio of the brittle fracture in this test piece is as follows.

$$(214+45\times 0.5)/(214+86+45)=68.6(\%)$$

The area ratio of the brittle fractures of all 50 test pieces of the tensile fracture surface after the stress corrosion resistance test was calculated for each condition of each of Examples and Comparative Examples, and a value obtained by dividing the total sum of the area ratios of respective brittle fractures by the number of test pieces, that is, 50, was considered as the area ratio of the brittle fracture.

$$\text{Area ratio of brittle fracture}=(d1+d2+\ldots+d50)/50$$

d-1. Gain Size of Sheet

Since the grain size of the sheet or the rod (wire) is affected largely by the sheet thickness or the wire diameter, it is necessary to measure the grain size in a state where the sheet thickness or the wire diameter of the material obtained by the completion of final cold-working is maintained. Thus, each sheet is cut to be halved at an arbitrary position in the longitudinal direction in the cross section of the sheet in the longitudinal direction passing through the sheet thickness center of the cross section of the sheet obtained by the completion of final cold-working which has a sheet thickness of 0.2 mm to 1.6 mm, thereby for preparing a sample. The cut length a (mm) was not particularly defined, but was five times or more of the sheet wideness. The surfaces of the samples were polished, and then, etched with aqueous ferric chloride solution, and the microstructures thereof were photographed. The schematic diagram is illustrated in FIG. 1.

When the number of points, in which the edge lines ((1) and (3)) and the center line ((2)) of the longitudinal direction of the cross section intersect with the grain boundary, is defined as n, the grain size d (mm) is determined by the following formula.

$$d=3\times a/n$$

The case where the existence ratio of the grains in which the grain size is (1/2) or more of the sheet thickness in the cross section in the longitudinal direction is 80% (0.8 times) or more of the cross-sectional area, and the average value of the grain sizes of grains of the sheets in which the grain size is equal to or more than the half of the sheet thickness (the average grain size of grains satisfying these sizes) is equal to or more than the sheet thickness is determined to be excellent and rated as "A"; the case where the existence ratio is 80% or more of the cross-sectional area and the average grain size is 80% or more of the sheet thickness and less than the sheet thickness is determined to be good and rated as "B"; and the case where the existence ratio is less than 80% of the cross-sectional area and/or the average grain size is less than 80% of the sheet thickness is determined to be poor and rated as "C".

According to the evaluation criteria, the results of evaluation on the grain size of Examples according to the present invention and Comparative Examples (sheets) are shown in Table 2-1 and Table 2-2.

d-2. Gain Size of Rod (Wire)

Since the grain size of the sheet or the rod (wire) is affected largely by the sheet thickness or the wire diameter, it is necessary to measure the grain size in a state where the sheet thickness or the wire diameter of the material obtained by the completion of final cold-working is maintained. Thus, each rod (wire) is cut to be halved at an arbitrary position in the longitudinal direction in the cross section of the rod (wire) in the longitudinal direction passing through the center of the cross section of the rod (wire) obtained by the completion of cold-wire-drawing which has a wire diameter of 0.63 mm to 1.79 mm, thereby for preparing a sample. The cut length a (mm) was not particularly defined, but five times or more of the diameter. The cross sections of the samples were polished, and then, etched with aqueous ferric chloride solution, and the microstructures thereof were photographed. In the same manner as in the sheet samples, the schematic diagram is illustrated in FIG. 1 and the grain size d (mm) is determined in the same manner as in the sheet samples.

The case where the existence ratio of the grains in which the grain size is (1/2) or more of the wire diameter in the cross section in the longitudinal direction is 80% (0.8 times) or more of the cross-sectional area, and the average value of the grain sizes of grains of the rods (wires) in which the grain size is equal to or more than the radius of the rod (wire) (the average grain size of grains satisfying these sizes) is equal to or more than the wire diameter is determined to be excellent and rated as "A"; the case where the existence ratio is 80% or more of the cross-sectional area and the average grain size is 80% or more of the wire diameter and less than the wire diameter is determined to be good and rated as "B"; and the case where the existence ratio is less than 80% of the cross-sectional area and/or the average grain size is less than 80% of the wire diameter is determined to be poor and rated as "C".

According to the evaluation criteria, the results of evaluation on the grain size of Examples according to the present invention and Comparative Examples (rods (wires)) are shown in Table 2-3 and Table 2-4.

e. Superelastic Characteristics [Residual Strain (%) after 6% Deformation]

A stress-strain curve (S-S curve) was determined by subjecting to a tensile test, and the residual strain was determined and evaluated. Five test pieces each having a length of 150 mm were cut out from each of the specimens and supplied to the test. The residual strain after 6% deformation was determined from the stress-strain curve (S-S curve), and the evaluation criteria are as follows.

Regarding the test conditions, the tensile test of alternately repeating strain loading and elimination by repeatedly loading predetermined strains of different levels over a gauge length of 25 mm, while temporarily increasing the amount of strain from 1% to 6% by 1% in each step, was carried out at a test rate of 2%/min. The cycle of strain loading used herein was as follows: as 0 MPa (strain at zero load)→1%→0 MPa→2%→0 MPa→3%→0 MPa→4%→0 MPa→5%→0 MPa→6%→0 MPa, the loading and unloading of the load were repeated by turns alternately, and while the strain at the time of loading was increased from 1% by 1% each, the loading and unloading of six strains were repeated till adding 6% of the loading strain.

The case where the residual strain was 0.5% or less, was judged to have excellent superelastic characteristics and was rated as "A"; the case where the residual strain was 1.0% or less but more than 0.5%, was judged to have satisfactory superelastic characteristics and was rated as "B"; and the case where the residual strain was large such as more than 1.0%, was judged to have unacceptable superelastic characteristics and was rated as "C".

According to the evaluation criteria, the results of evaluation on the superelastic characteristics of Examples according to the present invention and Comparative Examples (sheets and rods (wires)) are shown in Table 2-1 to Table 2-4.

For representative residual strains, stress-strain curves (S-S curve) are shown in FIGS. 6(a) and 6(b). FIG. 6(a) shows Example according to the present invention, which is a wrought material (a sheet, Example 13) which was subjected to the annealing treatment from the (α+β) phase temperature range to the β single-phase temperature range at a temperature-raising speed of 1.0° C./min, at an intermediate annealing temperature of 600° C., and a cumulative cold-working ratio of 90%. Contrary to the above, FIG. 6(b) shows Comparative Example, which is a wrought material (a sheet, Comparative Example 1) which was subjected to the annealing treatment from the (α+β) phase temperature range to the β single-phase temperature range at a temperature-raising speed of 30° C./min, at an intermediate annealing temperature of 500° C., and a cumulative cold-working ratio of 80%.

TABLE 1-1

| Alloy No. | Alloying additive elements (mass %) | | | Remarks |
|---|---|---|---|---|
| | Al | Mn | Others | |
| 1 | 8.1 | 10.7 | — | This invention |
| 2 | 8.1 | 11.1 | — | |
| 3 | 8.2 | 19.5 | — | |
| 4 | 8.1 | 5.5 | — | |
| 5 | 5.5 | 15.0 | — | |
| 6 | 9.5 | 11.0 | — | |
| 7 | 8.1 | 10.2 | Co 0.5 | |
| 8 | 8.1 | 10.2 | Fe 0.5 | |
| 9 | 8.1 | 8.0 | Ni 2.0 | |
| 10 | 2.0 | 11.0 | — | Comparative Example |
| 11 | 12.0 | 11.0 | — | |
| 12 | 8.0 | 4.0 | — | |
| 13 | 8.0 | 24.0 | — | |

Note:
'—' means not contained
The balance was Cu and unavoidable impurities

TABLE 1-2

| Alloy No. | Alloying additive elements (mass %) | | | | | | | | Remarks |
|---|---|---|---|---|---|---|---|---|---|
| | Al | Mn | Ti | V | Cr | Si | Sn | Zn | |
| 14 | 8.1 | 10.2 | 0.5 | — | — | — | — | — | This invention |
| 15 | 8.1 | 10.2 | — | 0.5 | — | — | — | — | |
| 16 | 8.1 | 10.2 | — | — | 0.5 | — | 0.1 | — | |
| 17 | 8.1 | 10.2 | — | — | — | 0.05 | — | — | |
| 18 | 8.1 | 10.2 | — | — | — | — | 0.5 | — | |
| 19 | 8.1 | 10.2 | — | — | — | — | — | 0.5 | |

Note:
'—' means not contained
The balance was Cu and unavoidable impurities

TABLE 2-1

| Remarks | Alloy No. | Working and heating process (cumulative working ratio [%], annealing temp. [° C.])* | Intermediate (α + β) retaining time period [min] | Temp.-raising speed (α + β) →β [° C./min] | β phase retaining time period [min] |
|---|---|---|---|---|---|
| Ex 1 | 1 | cumulative working ratio 30% | 60 | 5 | 10 |
| Ex 2 | 1 | cumulative working ratio 60% | 60 | 5 | 10 |
| Ex 3 | 1 | no annealing was done | 60 | 5 | 10 |
| Ex 4 | 1 | annealing temp. 400° C. | 60 | 5 | 10 |
| Ex 5 | 1 | cumulative working ratio 90%, annealing temp. 600° C. | 60 | 10 | 10 |
| Ex 6 | 1 | Standard | 30 | 5 | 10 |
| Ex 7 | 1 | Standard | 60 | 5 | 2 |
| Ex 8 | 1 | Standard | 60 | 5 | 120 |
| Ex 9 | 1 | Standard | 120 | 5 | 10 |
| Ex 10 | 1 | Standard | 60 | 1 | 10 |
| Ex 11 | 1 | cumulative working ratio 90%, annealing temp. 450° C. | 60 | 1 | 10 |
| Ex 12 | 1 | cumulative working ratio 90% | 60 | 1 | 10 |
| Ex 13 | 1 | cumulative working ratio 90%, annealing temp. 600° C. | 60 | 1 | 10 |
| Ex 14 | 1 | Standard | 60 | 10 | 10 |
| Ex 15 | 1 | Standard | 60 | 20 | 10 |

TABLE 2-1-continued

| Remarks | Alloy No. | Working and heating process | Intermediate (α + β) retaining time period | Temp.-raising speed (α + β) →β [° C./min] | β phase retaining time period [min] |
|---|---|---|---|---|---|
| Ex 16 | 1 | Standard | 60 | 5 | 10 |
| Ex 17 | 2 | Standard | 60 | 5 | 10 |
| Ex 18 | 3 | Standard | 60 | 5 | 10 |
| Ex 19 | 4 | Standard | 60 | 5 | 10 |
| Ex 20 | 5 | Standard | 60 | 5 | 10 |
| Ex 21 | 6 | Standard | 60 | 5 | 10 |
| Ex 22 | 7 | Standard | 60 | 5 | 10 |
| Ex 23 | 8 | Standard | 60 | 5 | 10 |
| Ex 24 | 9 | Standard | 60 | 5 | 10 |
| Ex 25 | 14 | Standard | 60 | 5 | 10 |
| Ex 26 | 15 | Standard | 60 | 5 | 10 |
| Ex 27 | 16 | Standard | 60 | 5 | 10 |
| Ex 28 | 17 | Standard | 60 | 5 | 10 |
| Ex 29 | 18 | Standard | 60 | 5 | 10 |
| Ex 30 | 19 | Standard | 60 | 5 | 10 |

| Remarks | Existence frequency of coincidence grain boundary Σ1 to 3 (%) | Existence frequency of coincidence grain boundary Σ1 to 29 (%) | Stress corrosion resistance [area ratio of brittle fracture surface %] | | Average grain size ratio [grain size/sheet thickness] | | Superelastic characteristics [residual strain (%) after 6% deformation] |
|---|---|---|---|---|---|---|---|
| Ex 1 | 42.5 | 50.2 | B | 7 | A | 1.1 | B |
| Ex 2 | 48.2 | 52.4 | A | 0 | A | 1.9 | A |
| Ex 3 | 41.9 | 49.8 | B | 8 | B | 0.8 | B |
| Ex 4 | 52.4 | 66.2 | A | 0 | A | 1.6 | A |
| Ex 5 | 40.1 | 47.8 | B | 8 | A | 1.2 | B |
| Ex 6 | 48.4 | 57.7 | A | 2 | A | 1.4 | B |
| Ex 7 | 48.2 | 60.4 | A | 3 | A | 1.5 | B |
| Ex 8 | 48.7 | 60.5 | A | 3 | A | 1.3 | B |
| Ex 9 | 49.2 | 59.1 | A | 1 | A | 1.4 | B |
| Ex 10 | 53.9 | 64.7 | A | 0 | A | 1.8 | A |
| Ex 11 | 72.3 | 87.2 | A | 0 | A | 2.4 | A |
| Ex 12 | 62.4 | 70.2 | A | 0 | A | 2.0 | A |
| Ex 13 | 54.1 | 65.4 | A | 0 | A | 1.8 | A |
| Ex 14 | 43.1 | 52.5 | B | 5 | A | 1.2 | B |
| Ex 15 | 41.3 | 46.2 | B | 9 | A | 1.3 | B |
| Ex 16 | 48.0 | 56.2 | A | 2 | A | 1.5 | B |
| Ex 17 | 49.2 | 57.3 | A | 2 | A | 1.4 | B |
| Ex 18 | 50.4 | 59.8 | A | 0 | A | 1.6 | B |
| Ex 19 | 44.7 | 52.6 | B | 7 | A | 1.1 | B |
| Ex 20 | 48.9 | 59.9 | A | 0 | A | 1.6 | B |
| Ex 21 | 51.7 | 61.5 | A | 0 | A | 1.6 | B |
| Ex 22 | 49.0 | 58.1 | A | 2 | A | 1.4 | B |
| Ex 23 | 49.3 | 61.2 | A | 0 | A | 1.5 | B |
| Ex 24 | 57.4 | 68.4 | A | 0 | A | 1.7 | A |
| Ex 25 | 47.3 | 59.1 | A | 0 | A | 1.5 | B |
| Ex 26 | 53.4 | 62.5 | A | 0 | A | 1.7 | B |
| Ex 27 | 48.6 | 59.3 | A | 3 | A | 1.5 | B |
| Ex 28 | 52.1 | 63.4 | A | 0 | A | 1.6 | B |
| Ex 29 | 48.2 | 59.3 | A | 2 | A | 1.3 | B |
| Ex 30 | 45.2 | 54.8 | B | 5 | A | 1.2 | B |

Note:
'Ex' means Example according to this invention.
*Standard (Standard conditions) means annealing at 500° C. for 60 min and cumulative cold-working ratio at 80%, and that/those changed from the standard conditions is/are described in the table.

TABLE 2-2

| Remarks | Alloy No. | Working and heating process (cumulative working ratio [%], annealing temp. [° C.])* | Intermediate (α + β) retaining time period [min] | Temp.-raising speed (α + β) →β [° C./min] | β phase retaining time period [min] |
|---|---|---|---|---|---|
| CEx 1 | 1 | Standard | 60 | 30 | 10 |
| CEx 2 | 1 | annealing temp. 700° C. | 60 | 5 | 10 |
| CEx 3 | 1 | annealing temp. 350° C. | impossible to be worked | | |
| CEx 4 | 1 | cumulative working ratio 20% | 60 | 5 | 10 |
| CEx 5 | 10 | Standard | 60 | 20 | 10 |
| CEx 6 | 11 | Standard | impossible to be worked | | |
| CEx 7 | 12 | Standard | impossible to be worked | | |
| CEx 8 | 13 | Standard | 60 | 20 | 10 |

TABLE 2-2-continued

| Remarks | Existence frequency of coincidence grain boundary Σ1 to 3 (%) | Existence frequency of coincidence grain boundary Σ1 to 29 (%) | Stress corrosion resistance [area ratio of brittle fracture surface %] | | Average grain size ratio [grain size/sheet thickness] | | Superelastic characteristics [residual strain (%) after 6% deformation] |
|---|---|---|---|---|---|---|---|
| CEx 1 | 7.8 | 19.8 | C | 26 | C | 0.3 | C |
| CEx 2 | 10.0 | 21.0 | C | 16 | C | 0.6 | C |
| CEx 3 | — | — | — | — | — | — | — |
| CEx 4 | 23.2 | 30.2 | C | 24 | C | 0.7 | C |
| CEx 5 | 28.2 | 33.4 | C | 19 | C | 0.6 | C |
| CEx 6 | — | — | — | — | — | — | — |
| CEx 7 | — | — | — | — | — | — | — |
| CEx 8 | 34.8 | 43.2 | C | 12 | C | 0.7 | C |

Note:
'CEx' means Comparative Example.
*Standard (Standard conditions) means annealing at 500° C. for 60 min and cumulative cold-working ratio at 80%, and that/those changed from the standard conditions is/are described in the table.
Note:
'—' means not determined (ND)

TABLE 2-3

| Remarks | Alloy No. | Working and heating process (cumulative working ratio [%], annealing temp. [° C.])* | Intermediate (α + β) retaining time period [min] | Temp.-raising speed (α + β) →β [° C./min] | β phase retaining time period [min] |
|---|---|---|---|---|---|
| Ex 31 | 1 | cumulative working ratio 30% | 60 | 1 | 10 |
| Ex 32 | 1 | cumulative working ratio 60% | 60 | 1 | 10 |
| Ex 33 | 1 | Standard | 60 | 1 | 10 |
| Ex 34 | 1 | cumulative working ratio 90% | 60 | 1 | 10 |
| Ex 35 | 2 | Standard | 60 | 5 | 10 |
| Ex 36 | 3 | Standard | 60 | 5 | 10 |
| Ex 37 | 4 | Standard | 60 | 5 | 10 |
| Ex 38 | 5 | Standard | 60 | 5 | 10 |
| Ex 39 | 6 | Standard | 60 | 5 | 10 |
| Ex 40 | 7 | Standard | 60 | 5 | 10 |
| Ex 41 | 8 | Standard | 60 | 5 | 10 |
| Ex 42 | 9 | Standard | 60 | 5 | 10 |
| Ex 43 | 14 | Standard | 60 | 5 | 10 |
| Ex 44 | 15 | Standard | 60 | 5 | 10 |
| Ex 45 | 16 | Standard | 60 | 5 | 10 |
| Ex 46 | 17 | Standard | 60 | 5 | 10 |
| Ex 47 | 18 | Standard | 60 | 5 | 10 |
| Ex 48 | 19 | Standard | 60 | 5 | 10 |
| Ex 49 | 1 | Standard | 60 | 5 | 10 |
| Ex 50 | 1 | Standard | 60 | 10 | 10 |
| Ex 51 | 1 | Standard | 60 | 20 | 10 |
| Ex 52 | 1 | annealing temp. 400° C. | 60 | 1 | 10 |
| Ex 53 | 1 | annealing temp. 600° C. | 60 | 1 | 10 |

| Remarks | Existence frequency of coincidence grain boundary Σ1 to 3 (%) | Existence frequency of coincidence grain boundary Σ1 to 29 (%) | Stress corrosion resistance [area ratio of brittle fracture surface %] | | Average grain size ratio [grain size/sheet thickness] | | Superelastic characteristics [residual strain (%) after 6% deformation] |
|---|---|---|---|---|---|---|---|
| Ex 31 | 41.3 | 46.8 | B | 8 | B | 0.9 | B |
| Ex 32 | 48.7 | 54.2 | A | 3 | A | 1.1 | A |
| Ex 33 | 54.7 | 62.4 | A | 0 | A | 1.4 | A |
| Ex 34 | 59.2 | 81.4 | A | 0 | A | 2.1 | A |
| Ex 35 | 48.6 | 55.2 | A | 2 | A | 1.3 | B |
| Ex 36 | 47.2 | 57.2 | A | 1 | A | 1.4 | B |
| Ex 37 | 43.5 | 51.3 | B | 7 | A | 1.2 | B |
| Ex 38 | 46.7 | 55.1 | A | 3 | A | 1.4 | B |
| Ex 39 | 48.3 | 57.3 | A | 1 | A | 1.2 | B |
| Ex 40 | 47.2 | 56.7 | A | 2 | A | 1.3 | B |
| Ex 41 | 48.4 | 59.8 | A | 1 | A | 1.1 | B |
| Ex 42 | 55.2 | 67.4 | A | 0 | A | 1.6 | A |
| Ex 43 | 47.4 | 56.4 | A | 1 | A | 1.2 | B |
| Ex 44 | 49.1 | 60.2 | A | 0 | A | 1.4 | B |
| Ex 45 | 42.3 | 46.8 | B | 6 | A | 1.5 | B |
| Ex 46 | 48.0 | 57.9 | A | 1 | A | 1.3 | B |
| Ex 47 | 47.6 | 58.1 | A | 0 | A | 1.5 | B |
| Ex 48 | 48.9 | 59.3 | A | 0 | A | 1.2 | B |

TABLE 2-3-continued

| | | | | | | | |
|---|---|---|---|---|---|---|---|
| Ex 49 | 48.2 | 55.9 | A | 0 | A | 1.3 | B |
| Ex 50 | 42.2 | 46.8 | B | 7 | B | 0.9 | B |
| Ex 51 | 40.2 | 45.4 | B | 9 | B | 0.8 | B |
| Ex 52 | 61.3 | 82.8 | A | 0 | A | 2.3 | A |
| Ex 53 | 51.7 | 60.4 | A | 2 | A | 1.4 | A |

Note:
*Standard (Standard conditions) means annealing at 500° C. for 60 min and cumulative cold-working ratio at 80%, and that/those changed from the standard conditions is/are described in the table.

TABLE 2-4

| Remarks | Alloy No. | Working and heating process (cumulative working ratio [%], annealing temp. [° C.])* | Intermediate (α + β) retaining time period [min] | Temp.-raising speed (α + β) →β [° C./min] | β phase retaining time period [min] |
|---|---|---|---|---|---|
| CEx 9 | 1 | Standard | 60 | 30 | 10 |
| CEx 10 | 1 | annealing temp. 700° C. | 60 | 5 | 10 |
| CEx 11 | 1 | annealing temp. 350° C. | | impossible to be worked | |
| CEx 12 | 1 | cumulative working ratio 20% | 60 | 5 | 10 |
| CEx 13 | 10 | Standard | 60 | 20 | 10 |

| Remarks | Existence frequency of coincidence grain boundary Σ1 to 3 (%) | Existence frequency of coincidence grain boundary Σ1 to 29 (%) | Stress corrosion resistance [area ratio of brittle fracture surface %] | | Average grain size ratio [grain size/sheet thickness] | | Superelastic characteristics [residual strain (%) after 6% deformation] |
|---|---|---|---|---|---|---|---|
| CEx 9 | 7.8 | 19.8 | C | 36 | C | 0.2 | C |
| CEx 10 | 8.5 | 19.3 | C | 26 | C | 0.5 | C |
| CEx 11 | — | — | — | — | — | — | — |
| CEx 12 | 33.2 | 41.2 | C | 15 | C | 0.6 | C |
| CEx 13 | 34.6 | 44.6 | C | 12 | C | 0.6 | C |

Note:
*Standard (Standard conditions) means annealing at 500° C. for 60 min and cumulative cold-working ratio at 80%, and that/those changed from the standard conditions is/are described in the table.
Note:
'—' means not determined (ND)

Examples 1 to 30 were the cases of the test results of rods (wires). Among Examples 1 to 21, Examples 1 to 16 were the cases of the test results in which the production process of the rods (wires) was changed with the representative alloy composition. Examples 17 to 21 were the cases of the test results in which the alloys were consisted of the essential alloying elements only and in which the contents (composition ratios) therefor were changed, to change the alloy compositions. Examples 22 to 30 were the cases of the test results in which the alloy compositions were changed to compose of the essentially adding alloying elements and optionally adding alloying element(s) (small amount-adding alloying element(s)) to be added.

Further, Examples 31 to 53 were the cases of the test results of sheets. Examples 31 to 34 and Examples 49 to 53, except Examples 35 to 48, were the cases of the test results in which the production process was changed with the representative alloy composition. Examples 35 to 39 were the cases of the test results in which the alloys were consisted of the essential alloying elements only and in which the contents (composition ratios) therefor were changed, to change the alloy compositions. Examples 40 to 48 were the cases of the test results in which the alloy compositions were changed to compose of the essentially adding alloying elements and optionally adding alloying element(s) (small amount-adding alloying element(s)) to be added.

As is apparent from the results shown in the tables, and as shown from the results of Examples 1 to 30 and 31 to 53, the wrought materials (sheets and rods), each of which satisfy the given coincidence grain boundary as defined in the present invention, can be obtained, by satisfying the preferred production conditions as in the present invention, and also making the alloy compositions to be within the preferred range of the present invention. Thus, the wrought materials were excellent in stress corrosion resistance and excellent in superelastic characteristics. In addition, the existence ratios of grains of Examples, in which the grain size was equal to or more than (1/2) of the sheet thickness or the diameter of the wrought material in the cross section in the longitudinal direction, were each 80% or more of the cross-sectional area of the cross section. The average grain size also satisfied the range of the present invention.

Contrary to the above, each of the Comparative Examples resulted in the results in which any of the characteristics was poor. Since the existence frequency of a predetermined coincidence grain boundary did not satisfy the range of the present invention, Comparative Examples 1, 2, 4, 5, 8, 9, 10, 12, and 13 were poor in stress corrosion resistance and superelastic characteristics. Since the Al content in Comparative Example 6 was too large and the Mn content in Comparative Example 7 was too small, the hot-working each were impossible to be carried out. Since the intermediate annealing temperatures in Comparative Examples 3 and 11 too were too low, working cracking occurred, and thus the cold-working was impossible to be carried out only at necessary working ratio. Herein, as seen in Comparative Examples 1 and 9, since the temperature-raising speeds from the (α+β) phase to the β phase in the shape-memory heat treatment step each were too fast, the coincidence grain boundary did not sufficiently develop. In Comparative Examples 2 and 10, since the annealing temperatures in the intermediate annealing each were too high, the coincidence grain boundary did not conspicuously develop. In addition, in Comparative Examples 4, 12, and the like, in which the cumulative working ratios in the working and heating step each were too low, similarly, the coincidence grain boundary did not develop, and the existence frequency of the coincidence grain boundary was conspicuously low. Further, regarding the material (alloy) composition, since the Al amounts in Comparative Examples 5 and 13 each were as low as 2% and the Mn amount in Comparative Example 8 was as high as 24%, the coincidence grain boundary did not conspicuously develop.

Regarding the grain sizes of these materials of Comparative Examples, there was no material satisfying the preferred range of the present invention, due to the influences of the temperature-raising speed in the shape-memory heat treatment step, the annealing temperature and the cumulative working ratio in the working and heating step, the material (alloy) composition, and the like.

Further, the test results were omitted but not shown. However, for the case of the wrought material of the present invention, which had the preferred alloy compositions within the range defined in the present invention other than those described in Tables 1-1 and 1-2, the similar results as those Examples can be obtained.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A wrought material comprised of a Cu—Al—Mn-based alloy, wherein the wrought material has an alloy composition comprising: 5 to 10 mass % of Al; 5 to 20 mass % of Mn; 2 mass % or less of Ni; and 10 mass % or less in total of at least one element selected from the group consisting of Co, Fe, Ti, V, Cr, Si, Nb, Mo, W, Sn, Mg, P, Be, Sb, Cd, As, Zr, Zn, and Ag, in which the at least one element is selected from the group consists of: Co 0.001 to 2 mass %, Fe 0.001 to 3 mass %, Sn 0.001 to 1 mass %, Ti 0.001 to 2 mass %, V, Nb, Mo and Zr respectively 0.001 to 1 mass %, Cr 0.001 to 2 mass %, Si 0.001 to 2 mass %, W 0.001 to 1 mass %, Mg 0.001 to 0.5 mass %, P 0.01 to 0.5 mass %, Be, Sb, Cd and As respectively 0.001 to 1 mass %, Zn 0.001 to 5 mass %, and Ag 0.001 to 2 mass %, with the balance being Cu and unavoidable impurities,
which is excellent in superelastic characteristics,
in which an existence frequency of a coincidence grain boundary with a Σ value of 3 or less is 35% or more but 75% or less,
in which an existence frequency of a coincidence grain boundary with a Σ value of 29 or less is 45% or more but 90% or less,
wherein a grain boundary with a Σ value of 29 or less is the coincidence grain boundary and a grain boundary with a Σ value of more than 29 is a random grain boundary, and
which has a recrystallized microstructure in which a proportion occupied by a β phase in the recrystallized microstructure is 98% or more,
wherein the wrought material is a rod, wherein an existence ratio of grains having a grain size of (½) or more of a sheet thickness or a wire diameter of the wrought material in a cross section in a longitudinal direction is 80% or more of the cross-sectional area, and wherein an average grain size of the grains is in the range of 0.8 times to 2.5 times more than the sheet thickness or the wire diameter of the wrought material,
wherein the wrought material is produced by a shape-memory heat treatment [Step 5] and by a working ratio of 20 to 90% in cold-working;
in which the shape-memory heat treatment [Step 5] includes:
[Step 5-1] of raising temperature from room temperature to the (α+β) phase temperature range by heating;
[Step 5-2] of retaining the (α+β) phase temperature range;
[Step 5-3] of heating from the (α+β) phase temperature range to the β single-phase temperature range at a predetermined slow temperature-raising speed;
[Step 5-4] of retaining the β single-phase temperature range; and
[Step 5-9] of quenching from the β single-phase temperature range;
wherein in the heating [Step 5-3], the temperature-raising speed at which the heating is performed from the (α+β) phase temperature range to the β single-phase temperature range is 20° C./min or less.

2. The wrought material comprised of a Cu—Al—Mn-based alloy as claimed in claim 1, which is excellent in stress corrosion resistance.

3. A correcting tool for ingrown toenail comprised of the wrought material of a Cu—Al—Mn-based alloy as claimed in claim 1.

4. An orthosis for hallux valgus comprised of the wrought material of a Cu—Al—Mn-based alloy as claimed in claim 1.

5. A structural member comprised of the wrought material of a Cu—Al—Mn-based alloy as claimed in claim 1.

6. A spectacle frame comprised of the wrought material of a Cu—Al—Mn-based alloy as claimed in claim 1.

7. An actuator comprised of the wrought material of a Cu—Al—Mn-based alloy as claimed in claim 1.

8. A connector comprised of the wrought material of a Cu—Al—Mn-based alloy as claimed in claim 1.

* * * * *